(12) United States Patent
Yu et al.

(10) Patent No.: US 7,067,525 B2
(45) Date of Patent: Jun. 27, 2006

(54) COMPOUNDS USEFUL AS MODULATORS OF MELANOCORTIN RECEPTORS AND PHARMACEUTICAL COMPOSITIONS COMPRISING SAME

(75) Inventors: Guixue Yu, Lawrenceville, NJ (US); John Macor, Guilford, CT (US); Timothy Herpin, Princeton, NJ (US); R. Michael Lawrence, Yardley, PA (US); George C. Morton, Collegeville, PA (US); Rejean Ruel, Saint-Lambert (CA); Graham S. Poindexter, Old Saybrook, CT (US); Edward H. Ruediger, Greenfield Park (CA); Carl Thibault, Mascouche (CA)

(73) Assignee: Bristol-Myers Squibb Co., Princeton, NJ (US)

( * ) Notice: Subject to any disclaimer, the term of this patent is extended or adjusted under 35 U.S.C. 154(b) by 8 days.

(21) Appl. No.: 10/696,761

(22) Filed: Oct. 29, 2003

(65) Prior Publication Data
US 2004/0229882 A1 Nov. 18, 2004

Related U.S. Application Data

(62) Division of application No. 10/090,288, filed on Mar. 4, 2002, now Pat. No. 6,713,487.

(60) Provisional application No. 60/273,206, filed on Mar. 2, 2001, provisional application No. 60/273,291, filed on Mar. 2, 2001.

(51) Int. Cl.
| | |
|---|---|
| A61K 31/44 | (2006.01) |
| A61K 31/445 | (2006.01) |
| C07D 401/04 | (2006.01) |
| C07D 413/04 | (2006.01) |
| C07D 211/70 | (2006.01) |

(52) U.S. Cl. .................. 514/278; 514/315; 546/18; 546/184

(58) Field of Classification Search ............ 546/18, 546/184; 514/278, 315
See application file for complete search history.

(56) References Cited

U.S. PATENT DOCUMENTS
| | | | |
|---|---|---|---|
| 5,559,128 A | 9/1996 | Chakravarty et al. | |
| 5,804,578 A | 9/1998 | Chakravarty et al. | |
| 5,919,777 A | 7/1999 | Hansen et al. | |

FOREIGN PATENT DOCUMENTS
| | | | |
|---|---|---|---|
| WO | WO97/83673 | * | 10/1997 |
| WO | WO 99/58501 | | 11/1999 |
| WO | WO 99/64002 | | 12/1999 |
| WO | WO 00/15657 | | 3/2000 |
| WO | WO 00/44770 | | 8/2000 |
| WO | WO 00/74679 | | 12/2000 |
| WO | WO 01/70708 | | 9/2001 |
| WO | WO 01/91752 | | 12/2001 |
| WO | WO 02/00654 | | 1/2002 |
| WO | WO 02/15909 | | 2/2002 |
| WO | WO 02/059107 | | 8/2002 |
| WO | WO 02/059108 | | 8/2002 |

* cited by examiner

Primary Examiner—Rita Desai
(74) Attorney, Agent, or Firm—Laurelee A. Duncan

(57) ABSTRACT

Compounds having the formula (I),

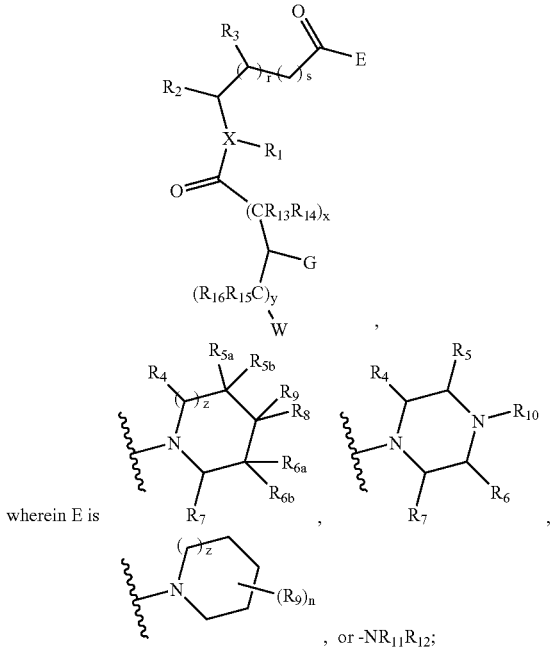

wherein E is , or $-NR_{11}R_{12}$;

G is a novel side chain selected from $C_{2-6}$alkenyl, $A_3$-aryl, $-OR_{18}$, heteroaryl, $A_1$-cyano, $A_2-OR_{17}$, $A_1-C(=O)R_{18}$, $A_1-CO_2R_{18}$, $A_1-C(=O)NR_{18}R_{19}$, $A_1-OC(=O)R_{18}$, $A_1-NR_{18}C(=O)R_{19}$, $A_1-OC(=O)NR_{18}R_{19}$, $A_1-NR_{18}CO_2R_{19}$, $A_1-NR_{18}SO_2R_{17}$, $A_1-SO_2R_{17}$, $A_1-NR_{20}C(=O)NR_{18}R_{19}$, and $A_1-SR_{18}$; or when y is 0 or when W is not $NHR_{22}$, G may be $A_1$-heterocyclo, wherein $A_1$ is a bond, $C_{1-6}$alkylene or $C_2$-alkenylene, $A_2$ is $C_{1-6}$alkylene or $C_{2-6}$alkenylene, and $A_3$ is $C_{2-6}$alkenylene; W is selected from $-NR_{21}R_{22}$, $-OR_{23}$, $-NR_{21}C(=O)R_{24}$, $-NR_{21}CO_2R_{24}$, amidino, guanidino, or a heteroaryl, heterocyclo or $C_{3-7}$cycloalkyl as defined in the specification, and X and $R_1$ through $R_{24}$ are as defined in the specification, are effective as modulators of melanocortin-receptors, particularly MC-1R and MC-4R.

14 Claims, No Drawings

COMPOUNDS USEFUL AS MODULATORS OF MELANOCORTIN RECEPTORS AND PHARMACEUTICAL COMPOSITIONS COMPRISING SAME

RELATED INVENTIONS

This application is a divisional of U.S. Ser. No. 10/090,288 filed Mar. 4, 2002 which claims priority to both U.S. Ser. Nos. 60/273,206 and 60/273,291 filed Mar. 2, 2001, the entire contents of which are incorporated herein by reference.

FIELD OF THE INVENTION

The present invention relates to compounds useful in treating diseases responsive to modulation of melanocortin receptors, to methods of treating such diseases, and to pharmaceutical compositions comprising same.

BACKGROUND OF THE INVENTION

Melanocortin peptides, particularly α-melanocyte stimulating hormone ((α-MSH), have a wide range of effects on biological functions including feeding behavior, pigmentation, and exocrine function. See Wikberg et al., "*New Aspects on the Melanocortins and their Receptors,*" *Pharmacological Research*, Vol. 42, No. 5 (2000), at pp. 393–420. The biological effects of α-MSH are mediated by a sub-family of G protein-coupled receptors, termed melanocortin receptors. See Wikberg et al., supra. There are four melanocortin receptors: MC-1R, MC-3R, MC-4R, and MC-5R (MC-2R is not a receptor for α-MSH but is the adrenocorticotropic hormone {ACTH} receptor). Activating any one of these receptors results in stimulation of cAMP formation.

MC-1R was first found in melanocytes. Naturally occurring inactive variants of MC-1R in animals were shown to lead to alterations in pigmentation and a subsequent lighter coat color. From these and other studies, it is evident that MC-1R is an important regulator of melanin production and coat color in animals (or skin color in humans). MC-3R is expressed in the brain and peripheral tissues, and knock-out studies have revealed that MC-3R is responsible for alterations in feeding behavior and body weight. MC-4R is primarily expressed in the brain. Genetic knock-outs and pharmacologic manipulation of MC-4R in animals have shown that agonizing MC-4R causes weight loss and antagonizing MC-4R produces weight gain. MC-5R is ubiquitously expressed in many peripheral tissues and in the brain, but its expression is greatest in exocrine glands. Genetic knock-out of this receptor in mice results in altered regulation of exocrine gland function, leading to changes in water repulsion and thermoregulation.

Much attention has been focused on the study of MC-3R and MC-4R modulators and their use in treating body weight disorders, such as obesity and anorexia. For example, WO 00/74679 to Merck & Co., Inc.,"Substituted Piperidines as Melanocortin-4-Receptor Agonists," (Dec. 14, 2000), and WO 99/64002 also to Merck & Co Inc., "Spiropiperidine Derivatives as Melanocortin Receptor Agonists," (Dec. 16, 1999), disclose compounds that reportedly are selective agonists of MC-4R. Each of the compounds of WO 00/74679 and WO 99/64002 has a bicyclic terminal group, typically tetrahydroisoquinoline. Isoquinoline compounds, more particularly tetrahydro-isoquinoline-based compounds, useful as melanocortin (MC) receptor agonists and antagonists are disclosed in U.S. Pat. No. 6,127,381, "Isoquinoline Compound Melanocortin Receptor Ligands and Method of Using Same," issued Oct. 3, 2000 to Basu et al. See also WO 01/91752, WO 01/70708, and WO 01/70337 to Merck and WO 02/00654 to Pfizer Products Inc., reportedly disclosing compounds for use as MC-4R agonists. Individual compounds can bind to multiple MC receptors, with different levels of affinity. Yet it is advantageous in treating diseases for compounds to be selective for one or more particular MC receptors. See, e.g., WO 00/58361 to Proctor & Gamble Co., "Melanocortin Receptor Ligands" (disclosing compounds that reportedly are selective for MC3R and MC4R in preference to MC-1R); and WO 99/54358 to Quadrant Holdings Cambridge Ltd., "Melanocortin Receptor Ligands" (disclosing compounds that reportedly are selective for MC3R, MC4R and/or MC5R).

The melanocortin peptides have potent physiological effects besides their role in regulating pigmentation, feeding behavior, and exocrine function. In particular, α-MSH has been shown to induce a potent anti-inflammatory effect in both acute and chronic models of inflammatory diseases including inflammatory bowel disease, renal ischemia/reperfusion injury, and endotoxin-induced hepatitis. See Catania et al., "*a-MSH in Normal Human Physiology and Disease States,*" *Trends in Endocrinology and Metabolism*, Vol. 11, No. 8 (2000) at pp. 304–308. Administration of α-MSH (either i.p. or i.v.) in these models results in substantial lessening of inflammation-mediated tissue damage, a significant decrease in leukocyte infiltration, and a dramatic reduction in elevated levels of cytokines (e.g., TNF-α), chemokines (e.g., MCP-1, IL-8), and inflammatory mediators (e.g., i-NOS and ICAM-1), to near baseline levels. Earlier studies had shown that α-MSH acts as an "anti-cytokine" in many acute inflammatory models, in effect antagonizing the pro-inflammatory actions of TNF-α, IL-1β, and IL-6.

The anti-inflammatory actions of α-MSH are mediated by MC-1R. MC-1R is expressed in cells that are important regulators of the immune response: monocyte/macrophages, neutrophils, endothelial, and mast cells. See Catania et al., cited above. Stimulation with α-MSH results in a dampening of the inflammatory response in these cells, including inhibition of nitric oxide formation, decreased expression of co-stimulatory molecules and adhesion receptors, and importantly, an increase in the expression of IL-10; a cytokine with potent anti-inflammatory actions. Studies have shown that MC-1R selective peptides are as efficacious as α-MSH in eliciting an anti-inflammatory response. See Wikberg, "*Melanocortin Receptors: Perspectives for Novel Drugs,*" *European Journal of Pharmacology*, Vol. 375 (1999), at pp. 295–310, and WO 99/57148 to WA Pharma AB (1999), "Melanocortin 1 Receptor Selective Compounds."

The mechanism by which agonism of MC-1R results in an anti-inflammatory response is likely through inhibition of the pro-inflammatory transcription activator, NF-κB. NF-κB is a pivotal component of the pro-inflammatory cascade, and its activation is a central event in initiating many inflammatory diseases. In a typical inflammatory response, NF-κB is activated in response to an inflammatory stimulus and once activated, induces expression of a wide array of pro-inflammatory genes. See Tak and Firestein, "*NF-κB: a Key Role in Inflammatory Diseases,*" *The Journal of Clinical Investigation*, Vol. 107 (2001), pp. 7–11. Activation of MC-1R, and subsequent generation of cAMP and/or decreased production of nitric oxide, has been shown to inhibit activation of NF-κB. See Manna and Aggarwal, "α-MSH Inhibits the Nuclear Transcription factor NF-κB Activation Induced by Various Inflammatory Agents," *The Journal of Immunology*, Vol. 161 (1998), pp. 2873–2880. Thus, α-MSH exerts anti-inflammatory actions through stimulation of MC-1R on cells involved in the inflammatory response and subsequent inhibition of the activation of the pro-inflammatory transcription factor NF-κB. Additionally, studies show that anti-inflammatory actions of α-MSH may be, in part, mediated by agonism of MC-3R and/or MC-5R. See WO 00/05263 to William Harvey Research Limited (2000), "Compounds for Use in the Treatment of Inflammation."

The present invention provides compounds useful as modulators of the melanocortin receptors, including selective modulators of MC-1R and/or MC-4R. Compounds that reportedly are selective agonists of MC-1R are disclosed in WO 99/57148, cited above, and selective antagonists of MC-1R are disclosed in WO 99/43709 to The Regents of the Univ. of Calif., "Melanocortin Receptor Antagonists and Modulations of Melanocortin Receptor Activity." Both WO 99/57148 and WO 99/43709 disclose large polypeptides. Small molecule inhibitors are advantageous in comparison to large polypeptides as they are less likely to induce immune reactions in patients and are more amendable to oral delivery. There remains a need for a small molecule useful as an MC-1R agonist, which is provided by the present invention. Melanocortin receptor modulators are also disclosed in U.S. patent application Ser. No. 10/090582, filed concomitantly herewith by the same inventors herein and assigned to the present assignee, claiming priority to U.S. patent applications Ser. Nos. 60/273,206, and 60/273,291, filed Mar. 2, 2001, the entire contents of which is incorporated herein by reference. Also incorporated herein is WO 99/58501 to Novo Nordisk.

SUMMARY OF THE INVENTION

The present invention is directed to compounds having the formula (I), useful as modulators of one or more melanocortin receptors,

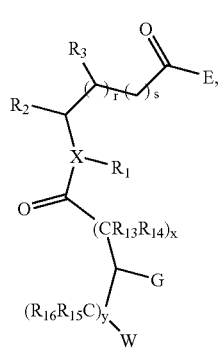

(I)

and pharmaceutically-acceptable salts, hydrates, or prodrugs thereof, in which:

X is N or CH;

$R_1$ is hydrogen or $C_{1-6}$alkyl or is taken together with $R_2$ or $R_3$ to form a monocyclic or bicyclic aryl, cycloalkyl, heteroaryl or heterocycle;

$R_2$ is hydrogen, aryl, cycloalkyl, heteroaryl, or heterocyclo; or $C_{1-6}$alkyl or $C_{2-6}$alkenyl optionally substituted with one to three of hydroxy, alkoxy, halogen, cyano, trifluoromethyl, nitro, amino, alkylamino, aryl, cycloalkyl, heteroaryl, and/or heterocyclo; or $R_2$ is taken together with $R_1$ or $R_3$ to form a monocyclic or bicyclic aryl, cycloalkyl, heteroaryl or heterocycle;

$R_3$ is hydrogen or $C_{1-6}$alkyl or is taken together with $R_2$ to form a monocyclic or bicyclic aryl, cycloalkyl, heteroaryl or heterocycle;

E is $E_1$, $E_2$, $E_3$ or $E_4$, wherein

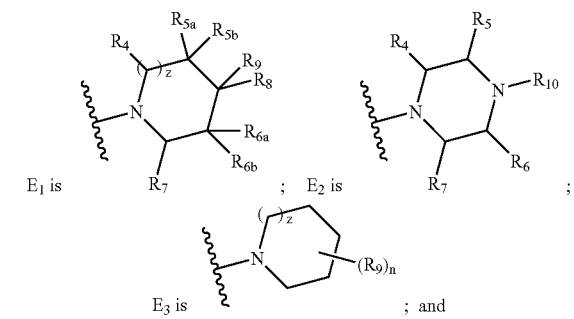

$E_4$ is $-NR_{11}R_{12}$;

G is selected from $C_{2-6}$alkenyl, $A_3$-aryl, $-OR_{18}$, heteroaryl, $A_1$-cyano, $A_2-OR_{17}$, $A_1-C(=O)R_{18}$, $A_1-CO_2R_{18}$, $A_1-C(=O)NR_{18}R_{19}$, $A_1-OC(=O)R_{18}$, $A_1-NR_{18}C(=O)R_{19}$, $A_1-OC(=O)NR_{18}R_{19}$, $A_1-NR_{18}CO_2R_{19}$, $A_1-NR_{18}SO_2R_{17}$, $A_1-SO_2R_{17}$, $A_1-NR_{20}C(=O)NR_{18}R_{19}$, and $A_1-SR_{18}$; or when y is 0, or when W is a group other than $NHR_{22}$, G may be $A_1$-heterocyclo, wherein $A_1$ is a bond, $C_{1-6}$alkylene or $C_{2-6}$alkenylene (straight or branched chain), $A_2$ is $C_{1-6}$alkylene or $C_{2-6}$alkenylene, and $A_3$ is $C_{2-6}$alkenylene;

W is selected from $-NR_{21}R_{22}$, $-OR_{23}$, $-NR_{21}C(=O)R_{24}$, $-NR_{21}CO_2R_{24}$, amidino, guanidino, or a substituted or unsubstituted heterocyclo, heteroaryl, or cycloalkyl selected from azepinyl, azetidinyl, imidazolyl, imidazolidinyl, pyrazolyl, pyridyl, pyrazinyl, pyridazinyl, 1,2-dihydropyridazinyl, pyranyl, tetrahydropyranyl, piperazinyl, homopiperazinyl, pyrrolyl, pyrrolidinyl, piperidinyl, thiazolyl, tetrahydrothiazolyl, thienyl, furyl, tetrahydrofuryl, morpholinyl, isoquinolinyl, tetrahydroisoquinolinyl, tetrazolyl, oxazolyl, tetrahydro-oxazolyl, and $C_{3-7}$cycloalkyl, wherein said heteroaryl, heterocyclo or cycloalkyl groups may additionally have joined thereto an optionally substituted five-to-seven membered heterocyclic, heteroaryl, or carbocyclic ring;

$R_4$ and $R_7$ are independently selected from hydrogen, alkyl, substituted alkyl, halogen, hydroxy, alkoxy, and keto;

$R_5$, $R_{5a}$, $R_{5b}$, $R_6$, $R_{6a}$, $R_{6b}$, $R_8$ and $R_9$ are independently hydrogen, halogen, cyano, alkyl, substituted alkyl, alkenyl, alkynyl, cycloalkyl, heterocyclo, aryl, heteroaryl, $-OR_{25}$, $-NR_{25}R_{26}$, $-SR_{25}$, $-S(O)_pR_{26}$, $-C(=O)R_{25}$, $-OC(=O)R_{25}$, $-CO_2R_{25}$, $-C(=O)NR_{25}R_{26}$, $-NR_{25}C(=O)R_{26}$, $-OC(=O)NR_{25}R_{26}$, $-NR_{25}CO_2R_{26}$, $-NR_{27}C(=O)NR_{25}R_{26}$ or $-NR_{25}SO_2R_{26}$; or $R_{5a}$ and $R_{5b}$, $R_{6a}$ and $R_{6b}$, or $R_8$ and $R_9$ taken together form a keto group (=O) or a monocyclic or bicyclic cycloalkyl or helerocyclo joined in a spiro fashion to ring E, or alternatively, $R_{5a}$ and/or $R_{5b}$ together with $R_8$ and/or $R_9$, or $R_{6a}$ and/or $R_{6b}$ together with $R_8$ and/or $R_9$, are taken to form a fused carbocyclic, heterocyclic, or heteroaryl ring; provided that, when G is a $C_{1-6}$alkyl substituted with $-OR_{17}$, $-CO_2R_{18}$, or $-C(=O)NR_{18}R_{19}$, then $R_{5a}$, $R_{5b}$, $R_{6a}$, and $R_{6b}$ are hydrogen;

$R_{10}$ is selected from hydrogen, alkyl, substituted alkyl, cycloalkyl, aryl, heteroaryl, and hetereocyclo;

$R_{11}$ is hydrogen or $C_{1-8}$alkyl;

$R_{12}$ is $C_{1-8}$alkyl, substituted $C_{1-8}$alkyl, or cycloalkyl;

$R_{13}$, $R_{14}$, $R_{15}$ and $R_{16}$ are selected independently of each other from hydrogen, alkyl, substituted alkyl, amino, alkylamino, hydroxy, alkoxy, aryl, cycloalkyl, heteroaryl, or heterocyclo, or $R_{13}$ and $R_{14}$, or $R_{15}$ and $R_{16}$, when attached to the same carbon atom, may join to form a spirocycloalkyl ring;

$R_{17}$ is alkyl, substituted alkyl, cycloalkyl, aryl, heterocyclo, or heteroaryl;

$R_{18}$, $R_{19}$, and $R_{20}$ are independently selected from hydrogen, alkyl, substituted alkyl, alkenyl, substituted alkenyl, aryl, heteroaryl, cycloalkyl, heterocyclo, or $C(=O)R_{28}$; or when G is $NH(C=O)R_{19}$, $R_{19}$ may be a bond joined to W to define a heterocyclo ring; provided, however, that when y is at least one, W is imidazolyl, indolyl, $-NR_{21}R_{22}$, or $-OR_{23}$, and G is $-NR_{18}C(=O)R_{19}$, then $R_{19}$ is not a $C_1$-alkyl having the substituent $-NR_{29}R_{31}$;

$R_{21}$ and $R_{22}$ are selected from hydrogen, alkyl, and substituted alkyl;

$R_{23}$ and $R_{24}$ are independently hydrogen, alkyl, substituted alkyl, aryl, heteroaryl, heterocyclo, and cycloalkyl;

$R_{25}$, $R_{26}$ and $R_{27}$ are independently hydrogen, alkyl, substituted alkyl, cycloalkyl, aryl, heterocyclo, or heteroaryl; or $R_{25}$ and $R_{26}$ may join together to form a heterocyclo or heteroaryl, except $R_{26}$ is not hydrogen when joined to a sulfonyl group as in $-S(O)_pR_{26}$ or $-NR_{25}SO_2R_{26}$;

$R_{28}$ is hydrogen, alkyl, or substituted alkyl;

$R_{29}$ and $R_{31}$ are selected from hydrogen, alkyl, haloalkyl, hydroxyalkyl, phenylalkyl, and alkoxycarbonylalkyl, or $R_{29}$ and $R_{31}$ taken together form a heterocyclo ring;

n is 0, 1, 2, 3 or 4;

p is 1, 2, or 3;

r and s are 0 or 1;

x is 0, 1, or 2;

y is 0, 1, 2, 3 or 4; and z is 0, 1, or 2.

The invention is further directed to pharmaceutical compositions comprising one or more compounds according to formula (I). The invention is further directed to methods of treating melanocortin-receptor associated conditions, as defined herein, as well as methods of agonizing or antagonizing the melanocortin receptors, more particularly, MC-1R and MC-4R. The invention is also directed more generally to small molecule inhibitors of MC-1R, and to methods of treating diseases responsive to inhibition of MC-1R using a small molecule according to the invention.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When a subscript is used with reference to an alkyl or other group, the subscript refers to the number of carbon atoms that the group may contain.

The term "substituted alkyl" refers to an alkyl group as defined above having one, two or three substituents selected from the group consisting of halo, amino, cyano, keto (=O), $-OR_a$, $-SR_a$, $NR_aR_b$, $-(C=O)R_a$, $-CO_2R_a$, $-C(=O)$ $NR_aR_b$, $-NR_aC(=O)R_b$, $NR_aCO_2R_b$, $-OC(=O)R_a$, $-OC(=O)NR_aR_b$, $-NR_cC(=O)NR_aR_b$, $NR_aSO_2R_c$, $SO_2R_d$, $SO_3R_d$, cycloalkyl, aryl, heteroaryl, or heterocycle, wherein the groups $R_a$, $R_b$, and $R_c$ are selected from hydrogen, $C_{1-6}$alkyl, aryl, heteroaryl, heterocycle, cycloalkyl, or $C_{1-6}$alkyl substituted with halogen, hydroxy, methoxy, nitro, amino, cyano, $-(C=O)H$, $-CO_2H$, $-(C=O)$alkyl, $-CO_2$alkyl, $-NH(alkyl)$, $-NH(cycloalkyl)$, $-N(alkyl)_2$, carboxy, acyl, $-C(=O)H$, $-C(=O)$phenyl, $-CO_2$-alkyl, cycloalkyl, $-(C=O)NH_2$, $-(C=O)NH(alkyl)$, $-(C=O)$ $NH(cycloalkyl)$, $-(C=O)N(alkyl)_2$, $-C(=O)-(CH_2)_{1-2}$ $NH_2$, $-C(=O)-(CH_2)_{1-2}NH(alkyl)$, $-C(=O)-(CH_2)_{1-2}$ $N(alkyl)_2$, $-NH-CH_2$-carboxy, $-NH-CH_2-CO_2$-alkyl, phenyl, benzyl, phenylethyl, or phenyloxy. The group $R_d$ may be selected from the same groups as $R_a$, $R_b$ and $R_c$ but is not hydrogen. Alternatively, the groups $R_a$ and $R_b$ may together form a heterocyclo or heteroaryl ring. It should be understood that when a substituted alkyl group is substituted with an aryl, cycloalkyl, heteroaryl, or heterocyclo, such rings are as defined below and thus may have one to three substituents as set forth below in the defintions for these terms.

When the term "alkyl" is used as a suffix following another specifically named group, e.g., arylalkyl, heteroarylalkyl, the term defines with more specificity at least one of the substituents that the substituted alkyl will contain. For example, arylalkyl refers to an aryl bonded through an alkyl, or in other words, a substituted alkyl group having from 1 to 12 carbon atoms and at least one substituent that is aryl (e.g., benzyl or biphenyl). "Lower arylalkyl" refers to substituted alkyl groups having 1 to 4 carbon atoms and at least one aryl substituent.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred. A substituted alkenyl or alkynyl will contain one, two, or three substituents as defined above for alkyl groups.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above. Substituted alkylene, alkenylene, and alkynylene groups may have substituents as defined above for substituted alkyl groups.

The term "alkoxy" refers to the group $OR_e$ wherein $R_e$ is alkyl, substituted alkyl, alkenyl, substituted alkenyl, alkynyl, substituted alkynyl, heterocycle, or cycloalkyl. Thus, an alkoxy includes such groups as methoxy, ethoxy, cyclopropyloxy, pyrrolidinyloxy, and so forth. The term "aryloxy" refers to the groups O(aryl) or O(heteraryl), wherein aryl and heteroaryl are as defined below.

The term "alkylthio" refers to an alkyl or substituted alkyl group as defined above bonded through one or more sulfur (—S—) atoms, e.g., —S (alkyl) or —S (alkyl-$R_a$).

The term "alkylamino" refers to an alkyl or substituted alkyl group as defined above bonded through one or more nitrogen (—$NR_f$—) groups, wherein $R_f$ is hydrogen, alkyl, substituted alkyl, or cycloalkyl.

The term "acyl" refers to an alkyl or substituted alkyl group as defined above bonded through one or more carbonyl {—C(=O)—} groups. When the term acyl is used in conjunction with another group, as in acylamino, this refers to the carbonyl group {—C(=O) } linked to the second named group. Thus, acylamino refers to —C(=O)$NH_2$, substituted acylamino refers to the group —C(=O)NRR, and acylaryl refers to —C(=O)(aryl).

The term "aminoacyl" refers to the group —$NR_f$C(=O)$R_g$, wherein $R_g$ is hydrogen, alkyl, or substituted alkyl, and $R_f$ is as defined above for alkylamino groups.

The term "halo" or "halogen" refers to chloro, bromo, fluoro and iodo.

The term "carboxy" when used alone refers to the group $CO_2H$. Carboxyalkyl refers to the group $CO_2R$, wherein R is alkyl or substituted alkyl.

The term "sulphonyl" refers to a sulphoxide group (i.e., —$S(O)_{1-2}$—) linked to an organic radical including an alkyl, alkenyl, alkynyl, substituted alkyl, substituted alkenyl, or substituted alkynyl group, as defined above. The organic radical to which the sulphoxide group is attached may be monovalent (e.g., —$SO_2$-alkyl), or bivalent (e.g., —$SO_2$-alkylene, etc.)

The term "amidino" refers to the group

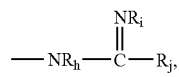

and the term "guanidino" refers to the group

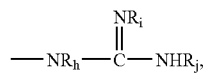

wherein for each of amidino and guanidino $R_h$, $R_i$, and $R_j$ may be hydrogen, alkyl, or substituted alkyl, or any two of $R_h$, $R_i$, and $R_j$ may join to form a heterocyclo or heteroaryl ring with the other of $R_h$, $R_i$, and $R_j$ comprising hydrogen, alkyl, or substituted alkyl.

The term "cycloalkyl" refers to substituted and unsubstituted monocyclic or bicyclic hydrocarbon groups of 3 to 9 carbon atoms which are, respectively, fully saturated or partially unsaturated, including a fused aryl ring, for example, an indan. A cycloalkyl group may be substituted by one or more (such as one to three) substituents selected from alkyl, substituted alkyl, aminoalkyl, halogen, cyano, nitro, trifluoromethyl, hydroxy, alkoxy, alkylamino, sulphonyl, —$SO_2$(aryl), —$CO_2H$, —$CO_2$-alkyl, —C(=O)H, keto, —C(=O)—$(CH_2)_{1-2}NH_2$, —C(=O)—$(CH_2)_{1-2}$NH(alkyl), —C(=O)—$(CH_2)_{1-2}$N(alkyl)$_2$, acyl, aryl, heterocylcle, heteroaryl, or another cycloalkyl ring of 3 to 7 carbon atoms. The term "cycloalkylene" refers to a cycloalkyl forming a link or spacer between two other groups, i.e., a cycloalkylene is a cycloalkyl that is bonded to at least two other groups. The term cycloalkyl includes saturated or partially unsaturated carbocyclic rings having a carbon-carbon bridge of three to four carbon atoms or having a benzene ring joined thereto. When the cycloalkyl group is substituted with a further ring, said further ring may have one to two substituents selected from $R_k$, wherein $R_k$ is lower alkyl, hydroxy, lower alkoxy, amino, halogen, cyano, trifluoromethyl, trifluoromethoxy, nitro, and lower alkyl substituted with one to two hydroxy, lower alkoxy, amino, halogen, cyano, trifluoromethyl, trifluoromethoxy, and/or nitro.

The term "aryl" refers to substituted and unsubstituted phenyl, 1-naphthyl and 2-naphthyl, with phenyl being preferred. The aryl may have zero, one, two or three substituents selected from the group consisting of alkyl, substituted alkyl, alkoxy, alkylthio, halo, hydroxy, nitro, cyano, amino, trifluoromethyl, trifluoromethoxy, sulphonyl, —$SO_2$(aryl), —NH(alkyl), —NH(cycloalkyl), —N(alkyl)$_2$, carboxy, acyl, —C(=O)H, —C(=O)phenyl, —$CO_2$-alkyl, cycloalkyl, —(C=O)$NH_2$, —(C=O)NH(alkyl), —(C=O)NH(cycloalkyl), —(C=O)N(alkyl)$_2$, —NH—$CH_2$-carboxy, —NH—$CH_2$—$CO_2$-alkyl, —C(=O)—$(CH_2)_{1-2}NH_2$, —C(=O)—$(CH_2)_{1-2}$NH(alkyl), —C(=O)—$(CH_2)_{1-2}$N(alkyl)$_2$, phenyl, benzyl, phenylethyl, phenyloxy, phenylthio, heterocyclo, heteroaryl, or a $C_{3-7}$cycloalkyl ring. The term "arylene" refers to an aryl as defined above forming a link or spacer between two other groups, i.e., an arylene is an aryl that is bonded to at least two other groups. When the aryl group is substituted with a further ring, said further ring may have one to two substituents selected from $R_k$, wherein $R_k$ is defined as above.

The term "carbocyclo" or "carbocyclic" refers to a cyclic group in which all ring atoms are carbon, including optionally-substituted cycloalkyl and aryl groups, as defined herein.

The term "heterocyclo" or "heterocycle" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain one, two or three substituents selected from the group consisting of halo, amino, cyano, alkyl, substituted alkyl, trifluoromethyl, trifluoromethoxy, sulphonyl, —SO2 (aryl), —NH(alkyl), —NH(cycloalkyl), —N(alkyl)$_2$, alkoxy, alkylthio, hydroxy, nitro, phenyl, benzyl, phenylethyl, phenyloxy, phenylthio, carboxy, —$CO_2$-alkyl, cycloalkyl, —C(=O)H, acyl, —(C=O)$NH_2$, —(C=O)NH(alkyl), —(C=O)NH(cycloalkyl), —(C=O)N(alkyl)$_2$, —NH—$CH_2$-carboxy, —NH—$CH_2$—$CO_2$-alkyl, —C(=O)—$(CH_2)_{1-2}NH_2$, —C(=O)—$(CH_2)_{1-2}$NH(alkyl), —C(=O)—$(CH_2)_{1-2}$N(alkyl)$_2$, heterocyclo, heteroaryl, a $C_{3-7}$cycloalkyl ring. keto, =N—OH, =N—O-lower alkyl, or a five or six membered ketal, i.e., 1,3-dioxolane or 1,3-dioxane. The heterocyclo ring may have a sulfur heteroatom that is substituted with one or more oxygen (=O) atoms, as for example, in

The term "heterocyclene" refers to a heterocycle as defined above forming a link or spacer between two other groups. When the heterocyclo group is substituted with a further ring, said further ring may have one to two substituents selected from $R_k$, wherein $R_k$ is defined as above.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain one, two or three substituents selected from the group consisting of halo, amino, cyano, alkyl, substituted alkyl, trifluoromethyl, trifluoromethoxy, sulphonyl, —$SO_2$(aryl), —NH(alkyl), —NH(cycloalkyl), —N(alkyl)$_2$, alkoxy, alkylthio, hydroxy, nitro, phenyl, benzyl, phenylethyl, phenyloxy, phenylthio, carboxy, —$CO_2$-alkyl, cycloalkyl, —C(=O)H, acyl, —(C=O)$NH_2$, —(C=O)NH(alkyl), —(C=O)NH(cycloalkyl), —(C=O)N(alkyl)$_2$, —NH—$CH_2$-carboxy, —NH—$CH_2$—$CO_2$-alkyl, —C(=O)—$(CH_2)_{1-2}NH_2$, —C(=O)—$(CH_2)_{1-2}$NH(alkyl), —C(=O)—$(CH_2)_{1-2}$N(alkyl)$_2$, heterocylco, heteroaryl, or a $C_{3-7}$cycloalkyl ring. The heterocyclo ring may have a sulfur heteroatom that is substituted with one or more oxygen (=O) atoms, as for example, in

The term "heteroarylene" or "heterarylene" refers to a heteroaryl as defined above forming a link or spacer between two other groups, i.e., it is a heteroaryl that is bonded to at least two other groups. When the heteroaryl group is substituted with a further ring, said further ring may have one to two substituents selected from $R_k$, wherein $R_k$ is defined as above.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

When reference is made herein to a particularly-named heterocyclic or heteroaryl group, such as azetidinyl, imidazolyl, piperazinyl, and so forth, the named ring may optionally contain one or more (preferably one to three) substituents selected from the substituents recited above for heteroaryl and heterocyclo groups, as appropriate. The term azetidinyl refers to an optionally-substituted four membered ring having one nitrogen heteroatom, i.e.,

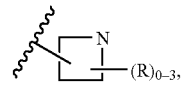

wherein R can be any substituent defined herein for heterocyclo groups and unless otherwise stated, the azetidinyl ring can be ttached to another group at any available carbon atom or at the nitrogen atom.

When reference is made to a particularly-named group having at least one heterocyclo, heteroaryl, or carbocyclic ring "joined" thereto, it is meant that two substituents attached to the same, adjacent, or non-adjacent atoms of the particularly-named group may join to form a second or third ring (i.e., the further ring may be fused, bridged or attached in a spiro fashion.) Each ring of these bicyclic or tricyclic groups may be optionally substituted, wherein the substituents are selected from those recited above for cycloalkyl, aryl, heterocyclo and heteroaryl groups. Thus, an imidazole having at least one ring joined thereto may include an aryl-fused imidazole such as benzimidazole having one or more (preferably one to three substituents), to an heteroaryl-fused imidazole such as a pyridoimidazole having one or more (preferably one to three) substituents, and so forth.

Accordingly, the above definitions and optional substituents for cycloalkyl, heterocyclo, and heteroaryl groups apply to spirocyclic ring systems. To illustrate, in compounds of formula (D) above, $R_8$ and $R_9$ are recited as optionally forming a spirocyclic ring. Thus, when z is 1, $R_8$ and $R_9$ together with the group E to which they are attached may be selected from the following exemplary groups, among others:

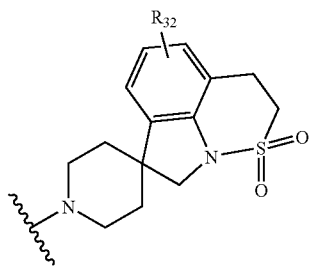

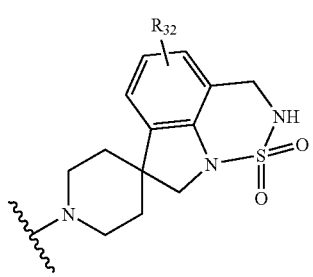

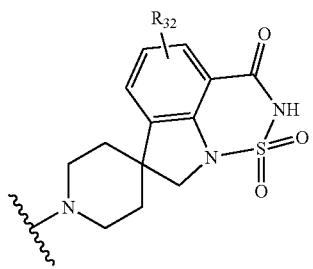

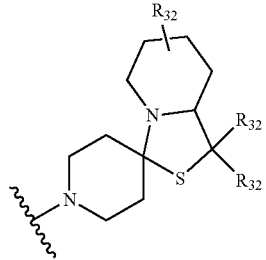

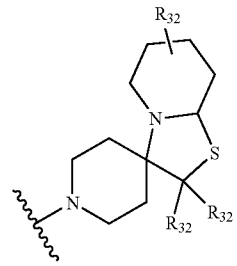

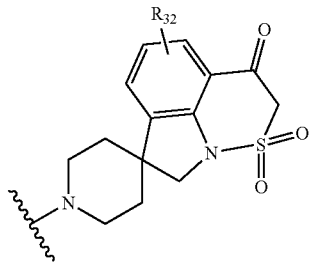

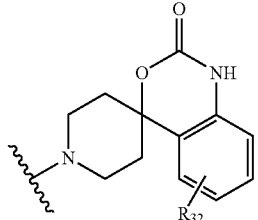

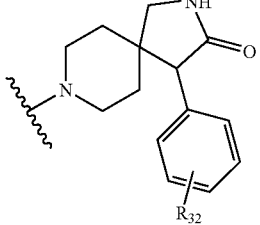

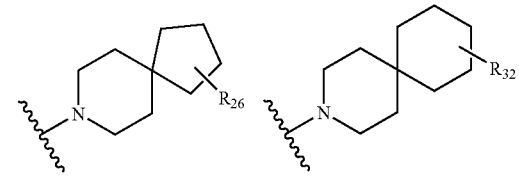

and

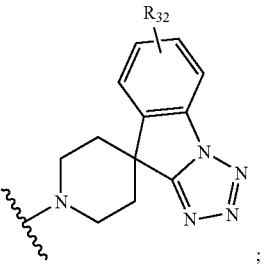

in which each $R_{32}$ group is hydrogen or selected from the above-recited substituents for aryl, cycloalkyl, heterocyclo and heteroaryl groups.

Additionally, one skilled in the field may make appropriate substitutions for the various groups of compounds of formula (I) herein, without departing from the spirit and scope of the invention. For example, it will be appreciated that in compounds of formula (I), the group E can be selected from, or replaced with, groups such as,

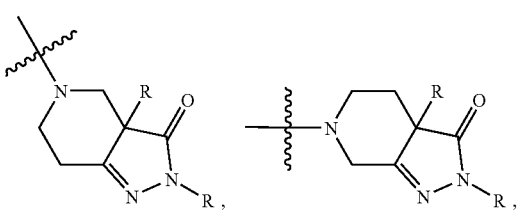

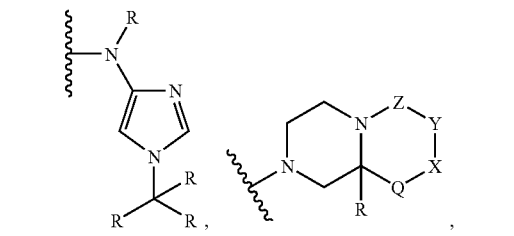

-continued

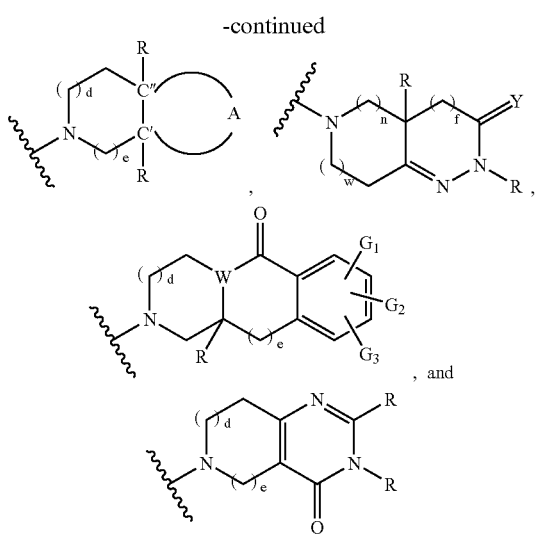

as defined in WO 02/00654 and WO 01/91752, wherein the various groups R, A, $G_{1-3}$, Q, W, X, Y, Z, d, e, f, n and w, may be selected from groups recited in WO 02/00654 and/or WO 01/91752, incorporated herein by reference.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also comtemplated as within the scope of the invention, e.g., they may be useful in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

The compounds of formula I which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of this invention are also contemplated herein. The term "prodrug", as employed herein, denotes a compound which, upon administration to a subject, undergoes chemical conversion by metabolic or chemical processes to yield a compound of the formula I, and/or a salt and/or solvate thereof. Solvates of the compounds of formula I are preferably hydrates.

Compounds of the formula I and salts thereof may exist in their tautomeric form (for example, as an amide or imino ether). All such tautomeric forms are contemplated herein as part of the present invention.

All stereoisomers of the present compounds, such as those, for example, which may exist due to asymmetric carbons, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

Methods of Preparation

The compounds of the present invention may be prepared by methods such as those illustrated in the following Schemes I to III. Starting materials are commercially available or can be readily prepared by one of ordinary skill in the art using known methods. For all of the schemes and compounds, the designated groups such as E, W, $R_8$, $R_9$, etc., are as described herein for a compound of formula I, unless otherwise indicated.

Solvents, temperatures, pressures, and other reaction conditions may readily be selected by one of ordinary skill in the art. Starting materials are commercially available or readily prepared by one of ordinary skill in the art. High Speed Analoging (HSA) may be employed in the preparation of compounds, for example, where the intermediates possess a carboxylic acid or amino group.

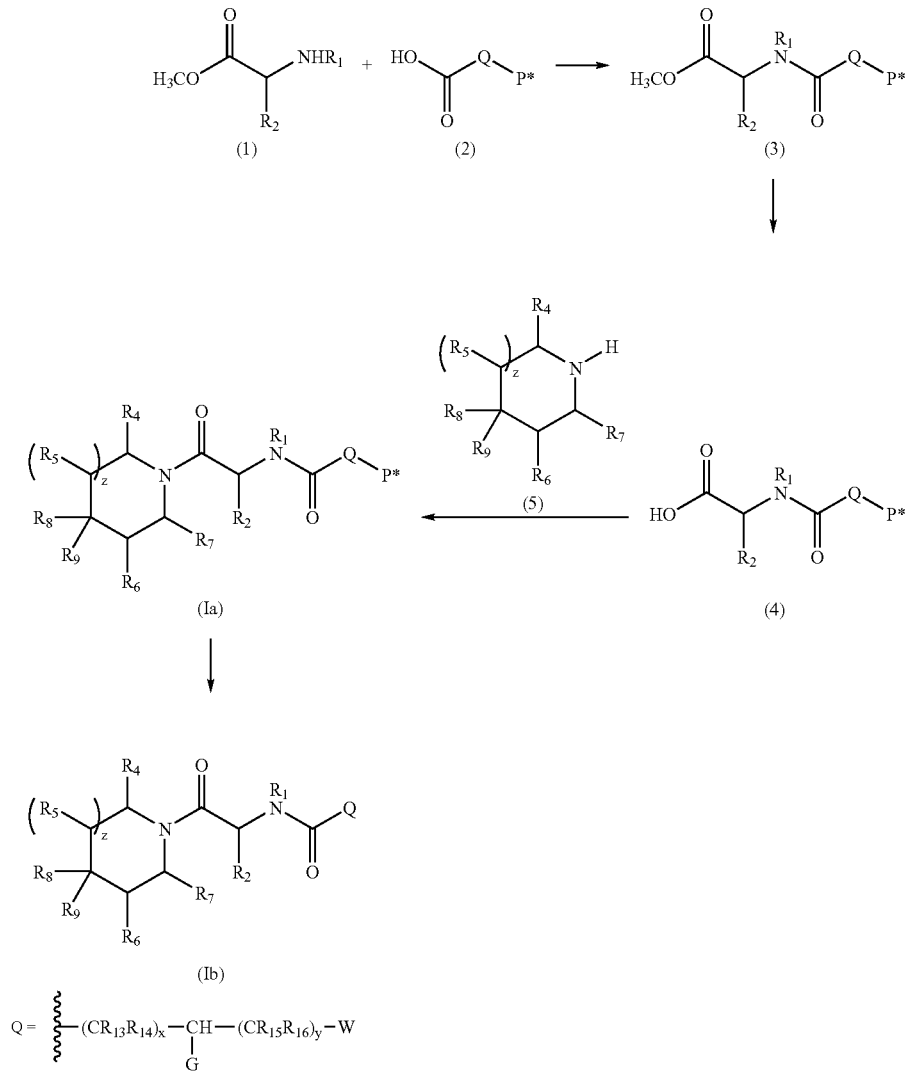

Scheme I (Ib)

$Q = \xi\!-\!(CR_{13}R_{14})_x\!-\!\underset{G}{CH}\!-\!(CR_{15}R_{16})_y\!-\!W$ Compounds of formula (Ib) can be prepared from compounds (Ia) [wherein P* is an amino protecting group, such as -Boc-, -CBZ-, -Fmoc-, which can be present in Q as in formula (Ia) or independently bonded to Q] via an appropriate amine deprotection process in an inert solvent at a temperature in the range −10° C. to 100° C. The choice of deprotection routes can be chosen by one of ordinary skill in the art. They include, but are not limited to TFA or hydrogen chloride acid for -Boc-, hydrogenation with an appropriate metal catalyst (such as Pd), for -CBZ-, or a base, such as NMM or DEA, for -Fmoc-. Inert solvents include, but are not limited to methylene dichloride, alcoholic solvents, THF, acetic acid, DMF, acetonitrile, and dioxane.

Compounds of formula (Ia) can be prepared by the coupling of compounds of formula (5) with compounds (4) using an appropriate carboxylic acid activating reagent in an inert solvent. Exemplary carboxylic acid activating agents include carbonyldiimidazole, dicyclohexylcarbodiimide, pentofluorophenol trifluoroacetate, 1-(3-dimethylaminopropyl)-3-ethylcarbodiimide, or other activating agents known by one of ordinary skill in the art. Exemplary inert solvents include ethers, including THF and dioxane, DMF, acetonitrile, or $CH_2Cl_2$.

Compounds (4) can be prepared by the hydrolysis of compounds (3) using a hydroxide source. Exemplary hydroxide sources include NaOH or LiOH. Exemplary solvents include water, alcohols, and mixtures of ethers/water.

Compounds (3) can be prepared by the coupling of compounds (1) and (2) using an appropriate carboxylic acid activating reagent in an inert solvent. Exemplary carboxylic acid activating agents include carbonyldiimidazole, dicyclohexylcarbodiimide, pentofluorophenol trifluoroacetate, 1-(3-dimethylaminopropyl)-3-ethylcarbodiimide, or other activating agents known by one of ordinary skill in the art. Exemplary inert solvents include ethers, including THF and dioxane, DMF, acetonitrile, or $CH_2Cl_2$.

Compounds (1), (2) and (3) are either commercially available or available by methods known to one of ordinary skill in the art.

Scheme II

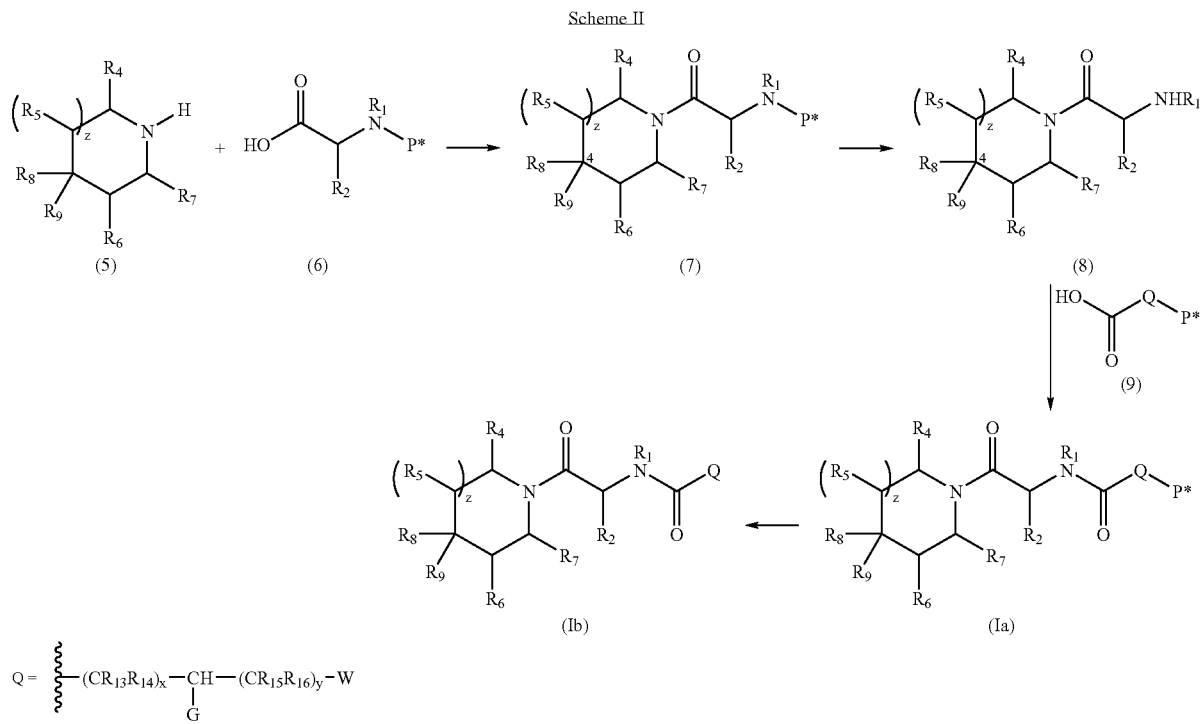

Compounds of formula (Ib) can be prepared from compounds of formula (Ia) [wherein P* is an amino-protecting group as in Scheme I] via an appropriate amine deprotection process in an inert solvent at a temperature in the range from −10° C. to 100° C. The choice of deprotection routes can be chosen by one of ordinary skill in the art. They include, but are not limited to TFA or hydrogen chloride acid for -Boc-, hydrogenation with an appropriate metal catalyst for -CBZ-, or a base, such as NMM or DEA, for -Fmoc-. Inert solvents include, but are not limited to methylene dichloride, alcoholic solvents, THF, acetic acid, DMF, acetonitrile, and dioxane.

Compounds of formula (Ia) can be prepared by the coupling of compounds (8) and (9) using an appropriate carboxylic acid activating reagent in an inert solvent. Exemplary carboxylic acid activating agents include carbonyldiimidazole, dicyclohexylcarbodiimide, pentofluorophenol trifluoroacetate, 1-(3-dimethylaminopropyl)-3-ethylcarbodiimide, or other activating agents known by on of ordinary skill in the art. Exemplary inert solvents include ethers, including THF and dioxane, DMF, acetonitrile, or $CH_2Cl_2$.

Compounds (8) [wherein P* is an amino-protecting group as above] can be prepared from compounds (7) via an appropriate amine deprotection process in an inert solvent at temperatures ranging from −10° C. to 100° C. The choice of deprotection routes can be chosen by one of ordinary skill in the art and include those referenced above in Scheme I for -Boc-, -CBZ-, and -Fmoc-. Inert solvents include, but are not limited to methylene dichloride, alcoholic solvents, THF, acetic acid, DMF, acetonitrile, and dioxane.

Compounds (7) can be prepared by the coupling of compounds (5) and (6) using an appropriate carboxylic acid activating reagent in an inert solvent. Exemplary carboxylic acid activating agents include carbonyldiimidazole, dicyclohexylcarbodiimide, pentofluorophenol trifluoroacetate, 1-(3-dimethylaminopropyl)-3-ethylcarbodiimide, or other activating agents known by one of ordinary skill in the art. Exemplary inert solvents include ethers, including THF and dioxane, DMF, acetonitrile, or $CH_2Cl_2$.

Compounds (5) and (6) are either commercially available or available by methods known to one of ordinary skill in the art.

Scheme III

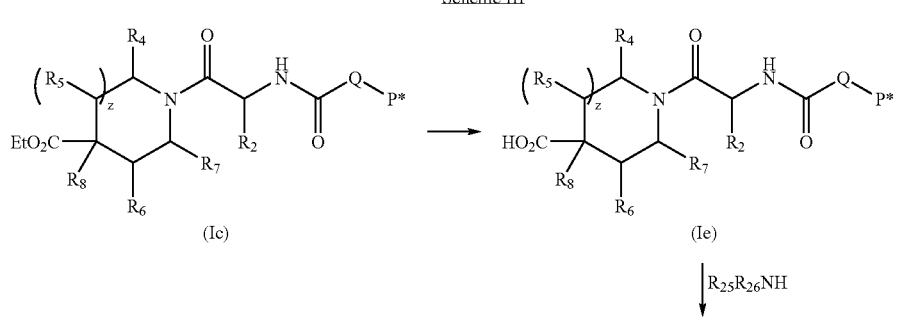

-continued

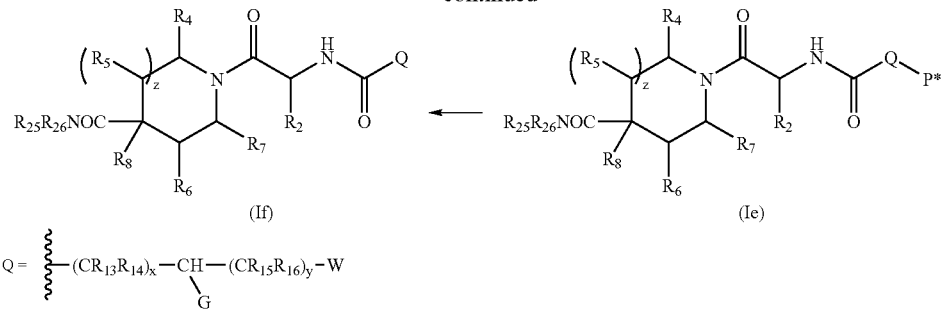

$Q = \{-(CR_{13}R_{14})_x-CH-(CR_{15}R_{16})_y-W$
                          |
                          G

Compounds of formula (If) can be prepared from compounds of formula (Ie) [wherein P* is an amino protecting group as in Scheme I] via an appropriate amine deprotection process chosen by one of ordinary skill in the art, such as described above in Schemes I and II.

Compounds of formula (Ie) can be prepared by the coupling of compounds of formula (Id) with amines of the formula $R_{25}R_{26}NH$ using an appropriate carboxylic acid activating reagent in an inert solvent. Exemplary carboxylic acid activating agents include carbonyldiimidazole, dicyclohexylcarbodiimide, pentofluorophenol trifluoroacetate, 1-(3-dimethylaminopropyl)-3-ethylcarbodiimide, or other activating agents known by one of ordinary skill in the art. Exemplary inert solvents include ethers, including THF and dioxane, DMF, acetonitrile, or $CH_2Cl_2$.

Compounds of formula (Id) can be prepared by the hydrolysis of compounds of formula (Ic) using a hydroxide source. Exemplary hydroxide sources include NaOH or LiOH. Exemplary solvents include water, alcohols, and mixtures of ethers/water.

Amines of the formula $R_{13}R_{14}NH$ are either commercially available or available by methods known to one of ordinary skill in the art. Compounds of formula (Ic) can be prepared as described above in Schemes I and II.

All documents cited in the present specification are incorporated herein by reference in their entirety.

Preferred Compounds

Preferred compounds are those having the formula,

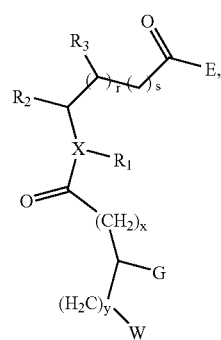

and pharmaceutically-acceptable salts, hydrates, or prodrugs thereof, in which:

X is N or CH;

$R_1$ is hydrogen or $C_{1-6}$alkyl or is taken together with $R_2$ or $R_3$ to form a monocyclic or bicyclic heteroaryl or heterocycle;

$R_2$ is hydrogen, aryl, cycloalkyl, heteroaryl, heterocyclo, or $C_{1-6}$alkyl or $C_{2-6}$alkenyl optionally substituted with one to three of hydroxy, halogen, aryl, cycloalkyl, heteroaryl, and/or heterocyclo; or $R_2$ is taken together with $R_1$ or $R_3$ to form a monocyclic or bicyclic aryl, cycloalkyl, heteroaryl or heterocycle;

$R_3$ is hydrogen or $C_{1-6}$alkyl or is taken together with $R_2$ to form a monocyclic or bicyclic aryl, cycloalkyl, heteroaryl or heterocycle;

E is $E_1$, $E_2$, $E_3$, or $E_4$, wherein

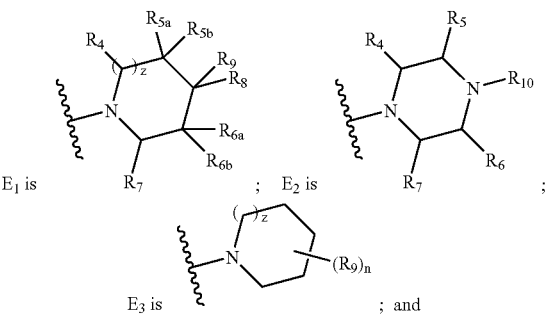

$E_4$ is $-NR_{11}R_{12}$;

G is selected from:

a) $C_{2-6}$alkenyl optionally substituted with phenyl;

b) $-OR_{18}$, $-C(=O)R_{18}$, $-CO_2R_{18}$, $-C(=O)NR_{18}R_{19}$, $-NR_{18}C(=O)R_{19}$, $-NR_{18}CO_2R_{19}$, $-NR_{18}SO_2R_{17}$, $-SO_2R_{17}$, $-NR_{20}C(=O)NR_{18}R_{19}$, and $-SR_{18}$, c) $C_{1-6}$alkyl or $C_{2-6}$alkenyl (straight or branched chain) substituted with at least one of cyano, $-OR_{17}$, $-C(=O)R_{18}$, $-CO_2R_{18}$, $-C(=O)NR_{18}R_{19}$, $-NR_{18}C(=O)R_{19}$, $-NR_{18}CO_2R_{19}$, $-NR_{18}SO_2R_{17}$, $-SO_2R_{17}$, $-NR_{20}C(=O)NR_{18}R_{19}$, and $-SR_{18}$; and d) when y is 0, G also may be selected from pyrrolidinyl, piperidinyl, pyrrolidinylalkyl, and piperidinylalkyl;

W is selected from $-NR_{21}R_{22}$, $-OR_{23}$, $-NR_{21}C(=O)R_{24}$, $-NR_{21}CO_2R_{24}$, amidino, guanidino, or a substituted or unsubstituted heterocyclo, heteroaryl, or cycloalkyl group selected from azetidinyl, imidazolyl, imidazolidinyl, pyrazolyl, pyridyl, pyrazinyl, pyridazinyl, 1,2-dihydropyridazinyl, pyranyl, tetrahydropyranyl, piperazinyl, homopiperazinyl, pyrrolyl, pyrrolidinyl, piperidinyl, thiazolyl, tetrahydrothiazolyl, thienyl, furyl, tetrahydrofuryl, morpholinyl, isoquinolinyl, tetrahydroisoquinolinyl, tetrazolyl, oxazolyl, tetrahydro-oxazolyl, and $C_{3-7}$cycloalkyl, wherein said heteroaryl, heterocyclo or cycloalkyl groups may additionally have joined thereto an optionally substituted five-to-seven membered heterocyclic, heteroaryl, or carbocyclic ring;

$R_4$ and $R_7$ are independently selected from hydrogen, alkyl, substituted alkyl, halogen, hydroxy, alkoxy, and keto;

$R_5$, $R_{5a}$, $R_{5b}$, $R_6$, $R_{6a}$, $R_{6b}$, $R_8$ and $R_9$ are independently hydrogen, halogen, cyano, alkyl, substituted alkyl, alkenyl, hydroxy, alkoxy, alkoxycarbonyl, acyl, cycycloalkyl, heterocyclo, aryl, or heteroaryl; or $R_{5a}$ and $R_{5b}$, $R_{6a}$ and $R_{6b}$, or $R_8$ and $R_9$ taken together form a keto group (=O) or a monocyclic or bicyclic cycloalkyl or heterocyclo joined in a spiro fashion to ring E, or alternatively, $R_{5a}$ and/or $R_{5b}$ together with $R_8$ and/or $R_9$, or $R_{6a}$ and/or $R_{6b}$ together with $R_8$ and/or $R_9$, are taken to form a fused benzene or heterocyclo ring; provided that, when G is a $C_{1-6}$alkyl substituted with —$OR_{17}$, —$CO_2R_{18}$, or —$C(=O)NR_{18}R_{19}$, then $R_{5a}$, $R_{5b}$, $R_{6a}$, and $R_{6b}$ are hydrogen;

$R_{10}$ is selected from hydrogen, alkyl, substituted alkyl, cycloalkyl, aryl, heteroaryl, and hetereocyclo;

$R_{11}$ is hydrogen or $C_{1-8}$alkyl;

$R_{12}$ is $C_{1-8}$alkyl, substituted $C_{1-8}$alkyl, or cycloalkyl;

$R_{17}$ is alkyl, substituted alkyl (e.g., benzyl), cycloalkyl, aryl, heterocyclo, or heteroaryl;

$R_{18}$, $R_{19}$, and $R_{20}$ are independently selected from hydrogen, alkyl, alkenyl, aryl, heteroaryl, cycloalkyl, heterocyclo, $C(=O)R_{28}$ or a $C_{1-4}$alkyl or $C_{2-4}$alkenyl substituted with one or more of aryl, heteroaryl, cycloalkyl, heterocyclo, alkoxycarbonyl, phenyloxy, and benzyloxy, and each of said ringed groups of $R_{18}$, $R_{19}$, and $R_{20}$ in turn is optionally substituted with one to two $R_{36}$;

$R_{21}$ and $R_{22}$ are selected from hydrogen, alkyl and substituted alkyl;

$R_{23}$ and $R_{24}$ are independently hydrogen, alkyl, substituted alkyl, aryl, heteroaryl, heterocyclo, and cycloalkyl;

$R_{28}$ is hydrogen, alkyl, or substituted alkyl;

$R_{36}$ is halogen, methoxy, nitro, phenyl, phenyloxy, or alkylamino;

n is 0, 1, 2, 3 or 4;

r and s are 0 or 1;

x is 0, 1, or 2;

y is 0, 1, 2, 3 or 4; and z is 0, 1, or 2.

In compounds of formula (I), preferably G is selected from $C_{2-6}$alkenyl optionally substituted with phenyl; —$OR_{17}$, —$C(=O)R_{18}$, —$CO_2R_{18}$, —$C(=O)NR_{18}R_{19}$, —$NR_{18}C(=O)R_{19}$, —$NR_{18}CO_2R_{19}$, —$SO_2R_{17}$, —$NR_{20}C(=O)NR_{18}R_{19}$, and —$SR_{18}$; and $C_{1-6}$alkyl or $C_{2-6}$alkenyl (straight or branched chain) substituted with at least one of cyano, —$OR_{17}$, —$C(=O)R_{18}$, —$CO_2R_{18}$, —$C(=O)NR_{18}R_{19}$, —$NR_{18}C(=O)R_{19}$, —$NR_{18}CO_2R_{19}$, —$SO_2R_{17}$, or —$NR_{20}C(=O)NR_{18}R_{19}$, and —$SR_{18}$; and when y is O, G also preferably may be selected from pyrrolidinyl, piperidinyl, pyrrolidinylalkyl, and piperidinylalkyl, wherein $R_{17}$ is lower alkyl, or optionally substituted phenyl or benzyl; $R_{18}$ and $R_{19}$ are as defined above, but preferably are hydrogen, lower alkyl, or optionally substituted phenyl or benzyl; and $R_{20}$ is hydrogen or lower alkyl.

More preferred are compounds where G is —$C_{2-4}$alkenyl, —$NHSO_2R_{17}$, or —$NHC(=O)R_{19}$, wherein $R_{17}$ and $R_{19}$ are lower alkyl or phenyl, or when W is imidazolyl, $R_{19}$ is taken together with W to form a heterocyclo ring. Most preferred are compounds where G is $NHC(=O)CH_3$.

In compounds of formula (I) herein, preferably W is selected from

—$NR_{21}R_{22}$, $NR_{21}C(=O)R_{24}$, and imidazolyl, wherein $R_{21}$, and $R_{22}$ are hydrogen or lower alkyl; $R_{34}$ is $C_{1-4}$alkyl; and u is 0 or 1. More preferably W is —$NH_2$, NH(lower alkyl), N(lower alkyl)$_2$, imidazolyl, or.

wherein $R_{34}$ is hydrogen or lower alkyl.

More preferred are compounds having the formula, wherein K is phenyl or thiazolyl, G is —$NR_{18}C(=O)R_{19}$, and $R_{18}$ and $R_{19}$ are hydrogen, lower alkyl, or phenyl; W is —$NH_2$, NH(lower alkyl), N(lower alkyl)$_2$, imidazolyl or wherein $R_{34}$ is hydrogen or lower alkyl; y is 0, 1, 2, 3 or 4, more preferably 1; $R_{30}$ is selected from $C_{1-4}$alkyl, hydroxy, alkoxy, halogen, nitro, cyano, amino, alkylamino, phenyl, and acylphenyl, more preferably chloro or methoxy; and E is a group selected from $E_1$, $E_2$, $E_3$, or $E_4$, recited above, but more preferably is

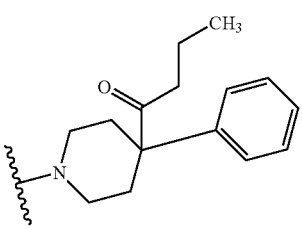
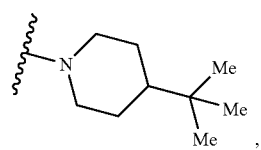
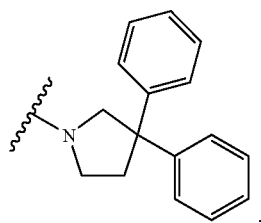
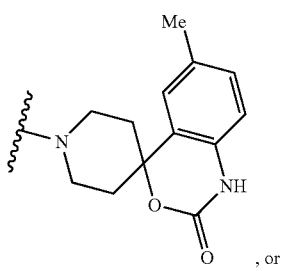, or
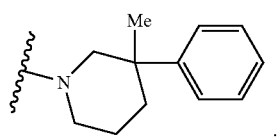.
Further preferred compounds are those having the formulae,
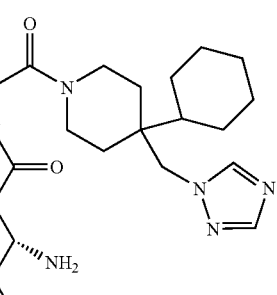
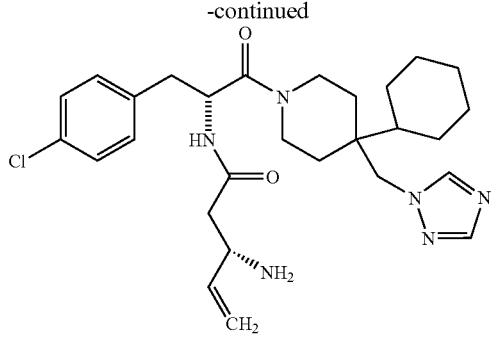
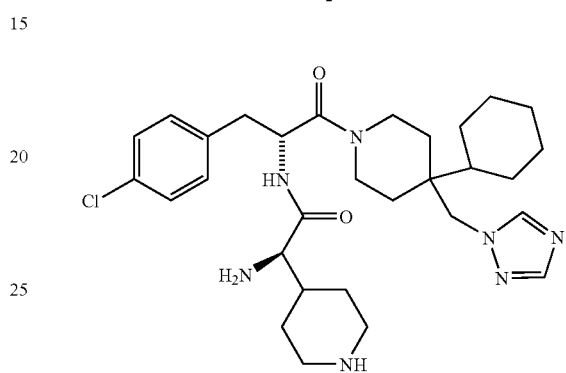
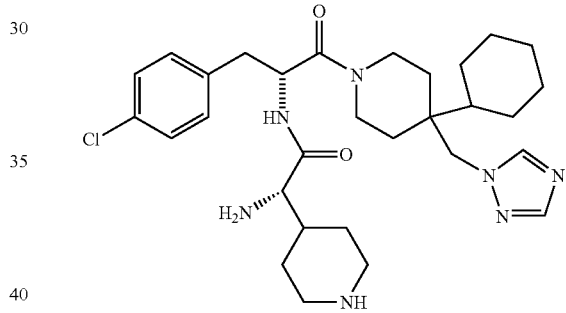
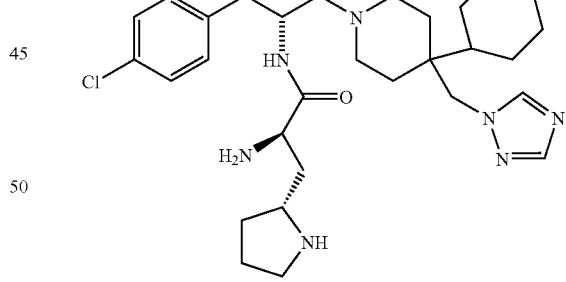
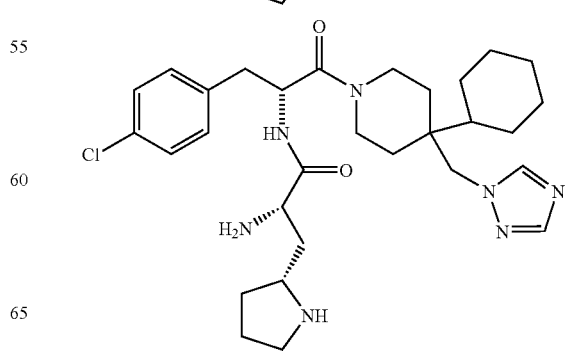

-continued
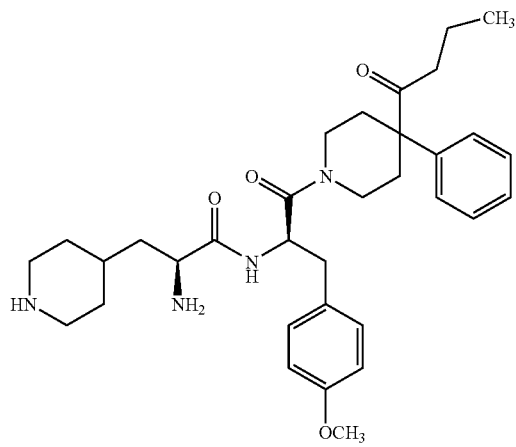
,
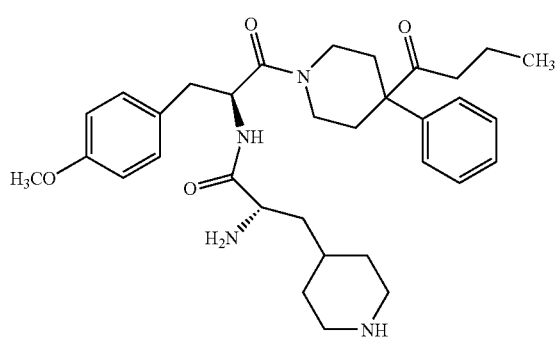
,
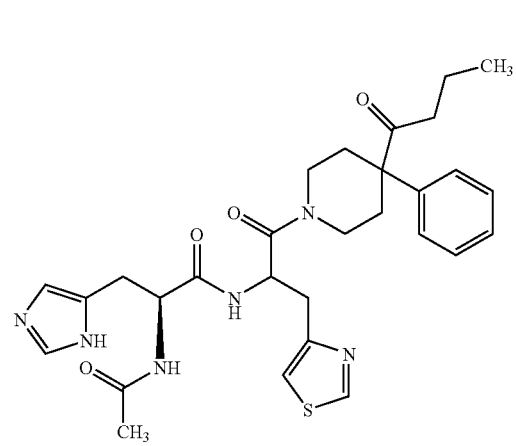
,
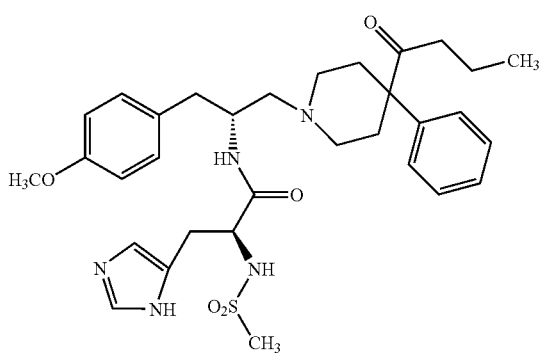
,
-continued
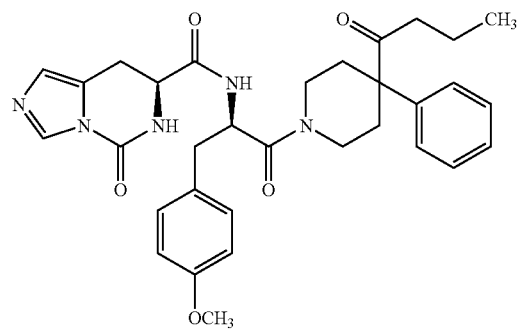
,
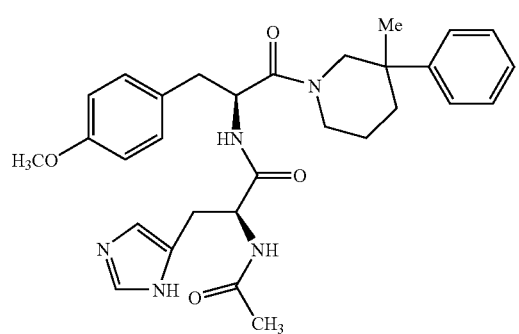
,
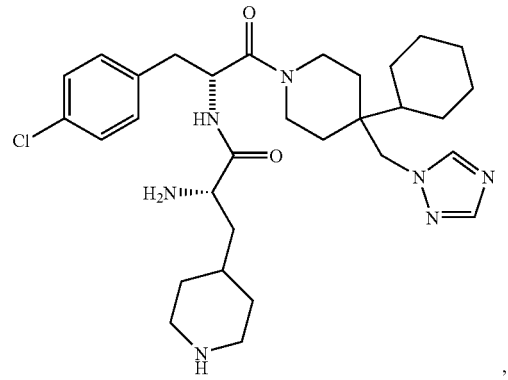
,
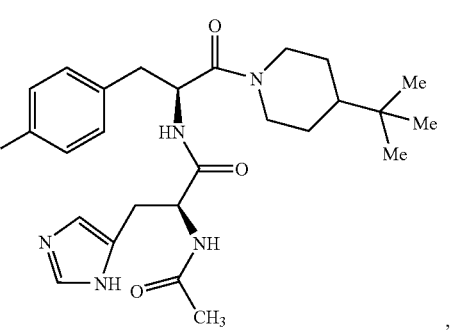
, -continued

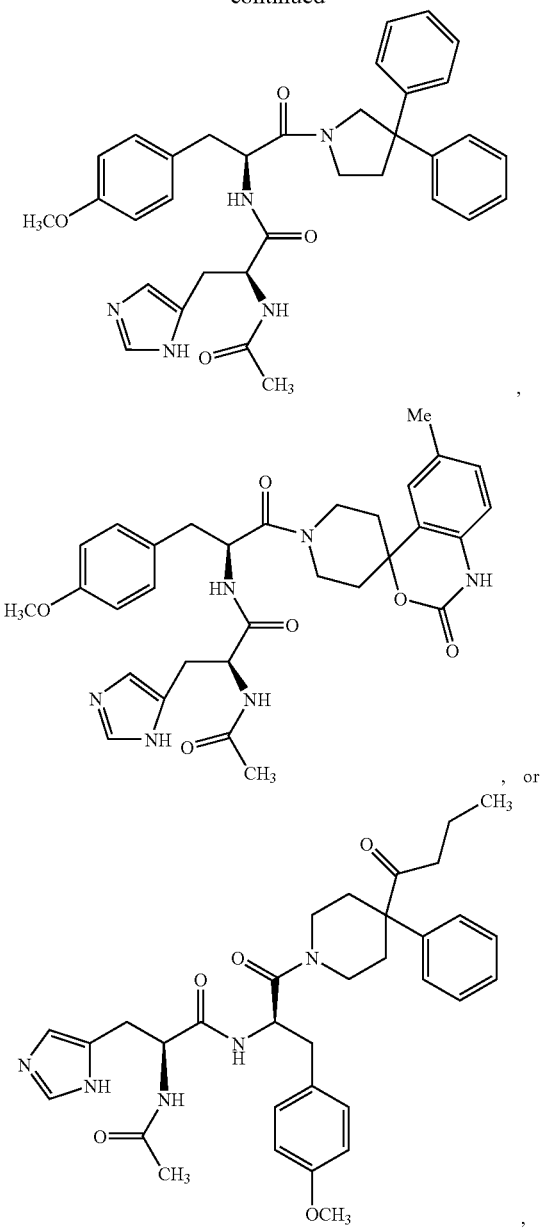

and pharmaceutically-acceptable salts, hydrates, and pro-drugs thereof.

Utility

The inventive compounds are modulators of the melanocortin receptors MC-1R, MC-3R, MC-4R, and/or MC-5R. The compounds are useful in treating a wide range of conditions responsive to regulation of the melanocortin receptors, including inflammatory and immune diseases, cardiovascular diseases, skin conditions, neurodegenerative conditions, sexual dysfunction, bodyweight disorders, and cancer. Certain compounds according to the invention have selective affinity for one melanocortin receptor relative to the other melanocortin receptors and thus are particularly useful for treating those diseases responsive to regulation of that receptor. For example, certain compounds have high selectivity for binding to MC-1R relative to MC-3R, MC-4R, and MC-5R, and those compounds are particularly useful in treating inflammatory or immune conditions. Certain other compounds according to the invention have high selective affinity for MC-4R and are particularly useful in treating bodyweight and/or neurodegenerative disorders. As used herein, the term "treating" or "treatment" refers to prophylaxis measures designed to inhibit or delay the onset of the disease or disorder and to responsive measures to alleviate, ameliorate, lessen, or cure the disease or disorder and/or its symptoms.

Compounds of the invention may be used to treat inflammation, particularly inflammation characterized by the activation of NF-κB and/or release of inflammatory cytokines. The compounds can be immunomodulators and have multiple effects on cells of the immune system. The compounds may be used to increase the levels of cAMP in cells (with resultant anti-inflammatory effects), decrease levels of the pro-inflammatory messenger nitric oxide, decrease chemotactic ability, and alter the expression of immune-related genes for such agents as cytokines, adhesion molecules, and nitric oxide synthase.

In view of their effects on inhibiting NF-κB activity and suppressing cytokine accumulation, the compounds will be useful in treating consequences of many diseases associated with chronic and acute inflammation and immune-modulation. Such diseases include, but are not limited to, inflammatory bowel disease, irritable bowel syndrome, gall bladder disease, Chrohn's disease, rheumatoid arthritis, osteoarthritis, osteoporosis, traumatic arthritis, rubella arthritis, muscle degeneration, pancreatis (acute or chronic), psoriasis, glomerulonephritis, serum sickness, lupus (systematic lupus erythematosis), urticaria, scleraclerma, schleroderma, chronic thyroiditis, Grave's disease, dermatitis (contact or atopic), dermatomyositis, alopecia, atopic eczemas, ichthyosis, fever, sepsis, migraine, cluster headaches, Alzheimer's Disease, Parkinson's disease, Creutzfeldt-Jacob disease, multiple sclerosis, tuberculosis, dementia, and transplant or graft-host rejections (e.g., kidney, liver, heart, lung, pancreas, bone marrow, cornea, small bowel, skin allografts, skin homografts and heterografts, etc.). The compounds may also be used to treat respiratory allergies and diseases including asthma, acute respiratory distress syndrome, hayfever, allergic rhinitis, and chronic obstructive pulmonary disease; and inflammatory disorders of the central nervous system, including HIV encephalitis, cerebral malaria, meningitis, and ataxia telangiectasis. Additionally, the compounds may be useful in treating pain, e.g., post-operative pain, neuromuscular pain, headache, pain caused by cancer, dental pain, and arthritis pain.

In view of their activity in inhibiting NF-κB activity, the compounds may be used to treat viral and autoimmune diseases including herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, autoimmune polyglandular disease (also known as autoimmune polyglandular syndrome), chronic active hepatitis or acute hepatitis infection (including hepatitis A, hepatits B, and hepatitis C), autoimmune gastritis, autoimmune hemolytic anemia, and autoimmune neutropenia. The compounds of the invention may also be used to treat fungal infections such as mycosis fungoides.

In addition, the compounds of this invention are useful in treating diseases of the cardiovascular system including those diseases in which inflammation is an underlying component. These diseases include but are not limited to atherosclerosis, transplant atherosclerosis, peripheral vascular disease, inflammatory vascular disease, intermittent claudication, restenosis, cerebrovascular stroke, transient ischemic attack, myocardial ischemia and myocardial infarction. The compounds also may be used to treat hypertension, hyperlipidemia, coronary artery disease, unstable angina, thrombosis, thrombin-induced platelet aggregation, and/or consequences occurring from thrombosis and/or the formation of atherosclerotic plaques.

Additionally, the compounds may be useful to treat stroke and other ischemic brain diseases and/or neurodegeneration associated therewith, and the neurodegeneration of, or consequences of, traumatic brain injury.

In view of their ability to act as immunomodulators in the skin and affect the production of melanin in the skin, the compounds are useful in altering pigmentation in the skin and may be used as photoprotective agents including agents for preventing, treating, or ameliorating sunburn. The compounds also may be used in treating acne, vitiligo, alopecia arreata, photosensitivity disorders, albinism, and porphyria. Addditionally, the compounds are useful to promote cosmetic as well as therapeutic tanning.

The compounds of the invention may also be used to treat neurodegenerative disorders including depression, anxiety, compulsion (obsessive-compulsive disorder), neuroses, psychosis, insomnia/sleep disorder, sleep apnea, and drug or substance abuse.

The compounds of the invention may be used to treat male or female sexual dysfunction. Male sexual dysfunction includes impotence, loss of libido, and erectile dysfunction (including but not limited to ejaculatory failure, premature ejaculation, or an inability to achieve or maintain an erection or inability to achieve an orgasm). Female sexual dysfunction may include sexual arousal disorder or disorders relating to desire, sexual receptivity, orgasm, and/or disturbances in trigger points of sexual function. Female sexual dysfunction may also include sexual pain, premature labor, dysmenorrhea, excessive menstruation, and endometriosis.

The compounds of the invention may also be used to treat bodyweight disorders including but not limited to obesity and anorexia (e.g., by altering appetite, metabolic rate, fat intake or carbohydrate craving); and diabetes mellitus (by enhancing glucose tolerance and/or decreasing insulin resistance).

The compounds also may be used to treat cancer, more particularly, cancer of the lung, prostate, colon, breast, ovaries, and bone, or angiogenic disorders including the formation or growth of solid tumors.

The compounds of the invention may also be used to treat veterinary disease such as veterinary viral infections, including feline immunodeficiency virus, bovine immunodeficiency virus, and canine immunodeficiency virus.

The term "melanocortin-receptor associated condition" when used herein refers to each of the above-referenced conditions, disorders, or diseases that may be treated by agonizing or antagonizing a melanocortin receptor, inhibiting NF-κB activity and/or suppressing cytokine accumulation as if each of these conditions, disorders and diseases were set forth herein at length.

The inventive compounds may be used alone or in combination with each other and/or other therapeutic agents such as anti-inflammatory drugs, antibiotics, anti-viral agents, anti-fungal agents, anti-diabetic agents, anti-osteoporosis agents, anti-obesity agents or appetite suppressants, growth promoting agents (including growth hormone secretagogues), anti-anxiety agents, anti-depressants, anti-hypertensive agents, cholesterol/lipid lowering agents, bone resorption inhibitors, and anti-tumor agents including antiproliferative agents, or cytotoxic drugs.

Examples of suitable other anti-inflammatory agents with which the inventive compounds may be used include aspirin, non-steroidal antiinflammatory drugs (NSAIDs) (such as ibuprofen and naproxin), TNF-α inhibitors (such as tenidap and rapamycin or derivatives thereof), or TNF-α antagonists (e.g., infliximab, OR1384), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), p38 mitogen-activated protein, kinase inhibitors, protein tyrosine kinase (PTK) inhibitors, IKK inhibitors, therapies for the treatment of irritable bowel syndrome (e.g., Zelmac® and Maxi-K® openers such as those disclosed in U.S. Pat. No. 6,184,231 B1), or other NF-κB inhibitors, such as corticosteroids, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; and nuclear translocation inhibitors, such as deoxyspergualin (DSG). To treat pain such as migraine and other headaches, the inventive compounds may be used in combination with aspirin, NSAIDs, or with $5\text{-HT}_{ID}$ receptor agonists such as sumitriptan, eletriptan or rizatriptan.

Examples of suitable other antibiotics with which the inventive compounds may be used include β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable other antifungal agents with which the inventive compounds may be used include fungal cell wall inhibitors (e.g., candidas), azoles (e.g., fluoconazole and vericonazole), and membrane disruptors (e.g., amphotericin B).

Examples of suitable other antiviral agents for use with the inventive compounds include nucleoside-based inhibitors, protease-based inhibitors, and viral-assembly inhibitors.

Examples of suitable anti-diabetic agents for use in combination with the compounds of the present invention include biguanides (e.g., metformin or phenformin), glucosidase inhibitors (e.g,. acarbose or miglitol), insulins (including insulin secretagogues, sensitizers or mimetics), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2), glucagon-like peptide-1 (GLP-1); dipeptidyl peptidase IV (DP4) inhibitors, Alistat®, Meridia®, and Zenacol®.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-obesity agents for use in combination with the compounds of the present invention include aP2 inhibitors, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin, adrenergic (and dopamine) reuptake inhibitor, such as sibutramine, topiramate (Johnson & Johnson) or axokine (Regeneron), other thyroid receptor beta drugs, such as a thyroid receptor ligand as disclosed in WO 97/21993 (U. Cal SF), WO 99/00353 (KaroBio) and GB98/284425 (KaroBio), and/or an anorectic agent (such as dexamphetamine, phentermine, phenylpropanolamine or mazindol). Additionally, the inventive compounds may be used with an α-gluocosidase inhibitor, an MHG—CoA reductase inhibitor, a sequestrant cholesteral lowering agent, a β3 adrenergic receptor agonist, a neuropeptide Y antagonist, or an α2-adrenergic receptor antagonist.

A still further use of the compounds of the invention is in combination with estrogen, testosterone, a selective estrogen receptor modulator, such as tamoxifen or raloxifene, or other androgen receptor modulators.

A further use of the compounds of this invention is in combination with steriodal or non-steroidal progesterone receptor agonists ("PRA"), such as levonorgestrel, medroxyprogesterone acetate (MPA).

Examples of suitable anti-anxiety agents for use in combination with the compounds of the present invention include benzodiazepines, diazepam, lorazepam, buspirone (Serzone®), oxazepam, and hydroxyzine pamoate, or dopamine recetpor agonists.

Examples of suitable anti-depressants for use in combination with the compounds of the present invention include citalopram, fluoxetine, nefazodone, sertraline, and paroxetine.

In treating skin disorders or diseases as described above, the compounds may be used alone or in combination with a retinoid, such as tretinoin, or a vitamin D analog.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone), renin inhibitors, ACE inhibitors (e.g., captopril, Vanlev®, pravachol, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and cardiac glycosides (e.g., digitalis and ouabain).

Examples of suitable cholesterol/lipid lowering agents for use in combination with the compounds of the present invention include HMG-CoA reductase inhibitors, squalene synthetase inhibitors, fibrates, bile acid sequestrants, ACAT inhibitors, MTP inhibitors, lipooxygenase inhibitors, an ileal $Na^+$/bile acid cotransporter inhibitor, cholesterol absorption inhibitors, and cholesterol ester transfer protein inhibitors (e.g., CP-529414).

In addition, the compounds may be used with other agents to increase the levels of cAMP or cGMP in cells for a therapeutic benefit. For example, applicants have discovered that MC-1R agonists including the compounds of the invention have advantageous effects when used in combination with phosphodiesterase inhibitors, including PDE1 inhibitors (such as those described in Journal of Medicinal Chemistry, Vol. 40, pp. 2196–2210 [1997]), PDE2 inhibitors, PDE3 inhibitors (such as revizinone, pimobendan, or olprinone), PDE4 inhibitors (such as rolipram, cilomilast, or piclamilast), and PDE7 inhibitors. The compounds of this invention also may be used in combination with PDE5 inhibitors such as sildenafil, sildenafil citrate, (e.g., when treating sexual dysfunction) or IC-351.

The combination of the inventive compounds with other therapeutic agents may prove to have additive and synergistic effects. The combination may be advantageous to increase the efficacy of the administration or decrease the dosage to reduce possible side-effects.

The compounds of formula I may be administered by any means suitable for the condition to be treated. The compounds may be delivered orally such as in the form of tablets, capsules, granules, powders, or with liquid formulations including syrups; sublingually; bucally; transdermally; parenterally such as by subcutaneous, intravenous, intramuscular, or intrasternal injection or infusion (e.g., as sterile injectable aqueous or non-aqueous solutions or suspensions); nasally such as by inhalation spray; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CAR- BOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. An exemplary effective amount of compounds of formula I may be within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses. Preferred subjects for treatment include animals, most preferably mammalian species such as humans, and domestic animals such as dogs, cats, horses, and the like, subject to melanocortin-receptor associated conditions.

Each of the inventive compounds exemplified herein has been tested and shown activity at a measurable level for modulating a melanocortin receptor, according to an assay described below and/or an assay known in the field, such as, for example, assays described in WO 00/74679 A1 and WO 01/91752.

Assays

MC1R

HBL cells, a human melanoma cell line licensed from Prof. G. Ghanem (Lab. of Oncology & Exp. Surgery, Free University of Brussels, Brussels, Belgium) were used as a source of the human MC-1R. cAMP was measured using the cAMP SPA Direct Screening Assay System from Amersham (RPA 559). 20,000 HBL cells were plated into each well of a half-area 96 well white plate and were used between 16–48 hours after plating. Cells were incubated at 37° C. for 15 minutes in 25 uM IBMX to inhibit phosphodiesterase activity. As per kit instructions, Assay Buffer Concentrate was diluted 1 to 50 with dH$_2$O to prepare Assay Buffer (50 mM acetate buffer containing 0.01% sodium azide). Vials containing rabbit anti-succinyl cAMP serum and the tracer, adenosine 3',5'-cyclic phosphoric acid 2'-0-succinyl-3-[$^{125}$I] iodotyrosine methyl ester, were resuspended with 7.5 ml Assay Buffer. SPA anti-rabbit reagent (donkey anti-rabbit IgG coupled to SPA PVT beads) was resuspended with 15 ml Assay Buffer. All reagents were stored at 4° C. after reconstitution. Melanocortin ligands or compounds were prepared in DMSO and added to the IBMX-treated cells as 100× concentrated stocks. 50 nM α-MSH was used for the maximum response and 1 ul DMSO was included in the negative control wells. The final concentration of DMSO was 1% in all the samples. After 15–30 minutes of stimulation, the reaction was terminated by the aspiration of the contents of the well followed by addition of 15 ul Assay Buffer containing 0.1 N HCl. Plates were kept at room temperature for at least 30 minutes to effect extraction of cAMP. Antiserum, Tracer, and SPA anti-rabbit reagent solutions were mixed 1:1:1 just prior to use. 15 ul of SPA reagent mixture was dispensed into each well and plates were incubated at room temperature for a minimum of 5 hours. Plates were subsequently counted for 6 minutes per sample in a TopCount scintillation reader with background subtraction. Data was analyzed in relation to a cAMP standard curve.

MC-4R

A. Binding Assay.

The membrane binding assay may be used to identify competitive inhibitors of [$^{125}$I]NDP-α-MSH binding to cloned human MC4R expressed in Hi5 insect cells infected by a baculovirus/human MC4R receptor construct.

Hi5 cells are grown in suspension in Express Five SFM Insect Cell Media (Gibco, Cat. No. 10486-025) at 27° C. with constant shaking. Hi5 cells are infected using the following protocol:

Cells at a density of 1×10$^6$ cells/mL are spun down at 1000 rpm (Beckman GS-6KR centrifuge) for 10 minutes.

Cells are resuspended in 10% of their original volume in a sterile 50 mL conical centrifuge tube wrapped with aluminum foil. Virus is added at a Multiplicity of Infection (MOI) of 3 and incubated for 1 hour at room temperature with gentle shaking.

This cell/virus mix is added to the appropriate volume of medium to attain the original volume and incubated at 27° C. with constant shaking for 72 hours.

Cells are spun down in 50 mL conical centrifuge tubes at 1000 rpm for 10 minutes. Each of the resulting pellets are resuspended in 10 mL of cold (4° C.) membrane buffer (25 mM HEPES, pH 7.4, 140 mM NaCl, 1.2 mM MgCl$_2$, 2.5 mM CaCl$_2$, 10 μG/mL Aprotinin, 10 μG/mL Leupeptin) and Dounce homogenized using 10–12 strokes. Dilute to 30 mL with buffer and centrifuge at 18,000 rpm, 4° C., 15 minutes (Sorvall RC5C Centrifuge). The resulting pellet is resuspended in cold membrane buffer in a total of ¼ of the original volume by vortexing and aspiration using a syringe and 27 gauge needle.

Protein content is determined (Bradford, Bio-Rad Protein Assay). Membranes are aliquoted in microcentrifuge tubes and quick frozen in liquid nitrogen. Store at –80° C. until use.

The membrane binding buffer is composed of 25 mM HEPES, pH 7.4, 140 mM NaCl, 1.2 mM MgCl$_2$, 2.5 mM CaCl$_2$, 0.1% BSA. 160 μL of membrane binding buffer containing 0.5 μg membrane protein is added to 20 μL of 1.0 nM [$^{125}$]-NDP-α-MSH (final concentration is 0.1 nM) and 20 μL of competing drug or buffer and incubated for 90 minutes at 37° C.

The mixture is filtered with Brandel Microplate 96 filter apparatus using 96-well GF/B filter presoaked in 1-% polyethyleneimine (Sigma). The filter is washed (4 times with a total of 1 mL per well) with cold wash buffer consisting of 20 mM HEPES, pH 7.4, 5 mM $MgCl_2$.

The filter is dried and punched into a 96 well sample plate (Wallac, 1450-401). 100 µl of Wallac Optiphase Supermix scintillation fluid is added to each well. The top is sealed and the plates are shaken to insure that the filters are thoroughly soaked with fluid. Plates are then counted in a Wallac Microbeta Trilux Scintillation and Luminescence Counter (Model 1450). Dose-response curves are fitted by linear regression analyses and $IC_{50}$ values are calculated using ExcelFit.

B. Functional assay.

Functional membrane based [$^{35}$S]GTPγS binding assays are developed to discriminate agonists and antagonists.

Membrane preparation. Cells (HEK-293 cells expressing the human MC4R) are grown in Minimum Essential Medium with Earle's salts and L-glutamate (Life Technologies, Cat. #11095-080) containing 10% heat-inactivated fetal bovine serum, 400 µg/mL geneticin and 100 mM sodium pyruvate in T175 flasks. Upon reaching confluence, cells are dissociated from tissue culture flasks by rinsing with $Ca^{2+}$ and $Mg^{2+}$ free phosphate buffered saline (Life Technologies, Cat. #14190-144) and detached following 5 minutes incubation at 37° C. with enzyme free cell dissociation buffer (Life Technologies, Cat. #13151-014). Cells are collected by centrifugation and resuspended in membrane preparation buffer consisting of 20 mM HEPES, pH 7.4, 10 mM EDTA, 10 µg/mL aprotinin and 10 µg/mL leupeptin. The suspension is homogenized by polytron PT3000 for 30 sec at 20,000 rpm, and centrifuged at 35,000×g for 15 minutes at 4° C. The pellet is resuspended in membrane preparation buffer and the last centrifugation is repeated. The final pellet is resuspended in membrane storage buffer consisting of 20 mM HEPES, pH 7.4, 0.1 mM EDTA, 10 µg/mL aprotinin and 10 µg/mL leupeptin. Protein concentration is determined by the Bio-Rad method (Bio-Rad, Cat.#500-0006) and the preparation is diluted to a final protein concentration of 1 mg/mL. Aliquots are stored at −70° C. until used.

[$^{35}$S]GTPγS membrane binding assay. Compounds are dissolved at 10 mM concentration in DMSO and diluted to the requited concentration into assay buffer. GTPγS to determine nonspecific binding is prepared at 100 µM concentration in assay buffer. The final concentration of DMSO in the assay is 1%. The assay buffer is consisting of 20 mM HEPES, pH 7.4, 100 mM NaCl, 5 mM $MgCl_2$, 0.5 µM GDP, 10 µg/mL saponin, 10 µg/mL aprotinin and 10 µg/mL leupeptin. The assay is composed by adding 50 µL 10× drug solution, 200 µL membrane preparation (containing 2–4 µg protein), 50 µL [$^{35}$S]GTPγS (100,000–150,000 CPM) and 200 µL assay buffer to achieve a total volume of 500 µL. The assay mixture is incubated at room temperature for exactly 30 minutes. The reaction is terminated by rapid filtration under vacuum through Whatman GF/B filters using a Brandel 96 wells cell harvester, followed by washing four times with cold wash buffer consisting of 20 mM HEPES, pH 7.4, and 5 mM $MgCl_2$. The filters are air-dried and 200 µL Wallac, Optiphase Super Mix, liquid scintillation cocktail is added to each filter. The bound radioactivity (CPM) is determined by Wallac Trilux 1450 MicroBeta liquid scintillation and Luminescence counter after six hours.

Data interpretation. NDP-α-MSH is used as reference compound and its maximal stimulation is measured at 1 µM (Ref CPM 100%). Total drug-independent binding (Total CPM) is measured in the absence of compounds. Response triggered by compounds is expressed as percent NDP-α-MSH response. Compound dose response curves are generated by Excel XL Fit. The top of the curve represents the compound's intrinsic activity expressed as % of maximal stimulation.

C. Radioligand Binding Assays.

Binding of [$^{125}$I]-(Nle$^4$, D-Phe$^7$)-α-MSH to human melanocortin receptors was performed using membrane homogenates from Hi5 cells that express recombinant MC4 receptors (Hi5-MC4 cells) and from HEK-293 cells that express recombinant MC3 receptors (HEK-MC3 cells) or MC5 receptors (HEK-MC5 cells) as well as from HBL cells expressing the human MC1R receptor. Homogenates (~0.5 µg protein/well) were incubated with [$^{125}$I]-(Nle$^4$,D-Phe$^7$)-α-MSH (100 pM for assays with MC4 receptors and 50 pM for assays with MC3/5 receptors) and increasing concentrations of competitors (final concentration of DMSO=1%) for 90 min at 37° C. in buffer consisting of 25 mM HEPES (pH 7.4), 140 mM NaCl, 2.5 mM $CaCl_2$, 1.2 mM $MgCl_2$ and 0.1% BSA (10 µg/ml aprotinin and 10 µg/ml leupeptin were added to assays with MC3/5 receptors). Assays were stopped by addition of cold wash buffer (20 mM HEPES and 5 mM $MgCl_2$ for assays with MC4 receptors and 20 mM HEPES for assays with MC3/5 receptors). Filtration over glass fiber filters (Whatman GF/B previously soaked in 1% PEI for assays with MC4 receptors or 0.5% PEI for assays with MC3/5 receptors) was performed using a Brandel cell harvester. Non-specific binding was defined with 1 µLM NDP-α-MSH.

The following Examples illustrate embodiments of the inventive compounds and starting materials, and are not intended to limit the scope of the claims. For ease of reference, the following abbreviations are used herein:

Abbreviations
Boc=tert-butoxycarbonyl
CBZ=benzyloxycarbonyl
DEA=diethylamine
DMAP=4-dimethylaminopyridine
DMF=N,N-dimethylformarnide
DMSO=dimethylsulfoxide
EDC=3-ethyl-3'-(dimethylamino)propyl-carbodiimide hydrochloride
Et=ethyl
EtOH=ethanol
EtOAc=ethyl acetate
FMOC=fluorenylmethoxycarbonyl
HOBT=1-hydroxybenzotriazole hydrate
NMM=N-methylmorpholine
Me=methyl
MeOH=methanol
mp=melting point
Ph=phenyl
THF=tetrahydrofuran
TFA=trifluoroacetic acid
tlc=thin layer chromatography
RT=room temperature
h=hours
HCl=hydrogen chloride
mmol=millimole
$Et_3N$=triethylamine
EtOAc=ethyl acetate
$Et_2O$=diethyl ether
$Na_2SO_4$=sodium sulfate
NaOH=sodium hydroxide
LiOH=lithium hydroxide
$CH_2Cl_2$=methylene chloride
HPLC=high pressure liquid chromatography
LRMS=low resolution mass spectrometry In the examples, when a letter is used in a superscript following the data, such as 3.28$^a$, the letter denotes the conditions used for the HLPC/MS, as follows:

Method A: Column Primesphere C18-HC 4.6×30 mm, gradient time: 2 minutes, Hold time: 1 minutes, Flow rate: 4 mL/min, Detector Wavelength: 220 nM, Solvent A=10% AcCN/90% H$_2$O/5mM NH$_4$OAc, Solvent B=90% AcCN/10% H$_2$O/5mM NH$_4$OAc, Start % B=0/Finish % B=100;

Method B: Column Primesphere C18-HC 4.6×30 mm, gradient time: 2 minutes, Hold time: 1 minutes, Flow rate: 4 mL/min, Detector Wavelength: 220 nM, Solvent A: 10% AcCN/90% H$_2$O/0.1% TFA, Solvent B: 90% AcCN/10% H$_2$O/0.1% TFA, Start % B=0/Finish % B=100;

Method C: Column Primesphere C18-HC 4.6×30 mm, gradient time: 3 minutes, Hold time: 1 minutes, Flow rate: 4 mL/min, Detector Wavelength: 220 nM, Solvent A: 10% AcCN/90% H$_2$O/0.1% TFA, Solvent B: 90% AcCN/10% H$_2$O/0.1% TFA, Start % B=0/Finish % B=100.

EXAMPLE 1

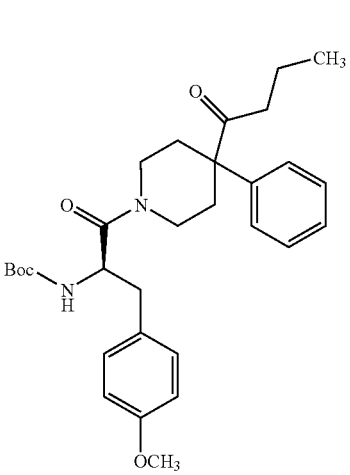

Step A:

(1A)

To a solution of N-Boc-D-4-methyltyrosine

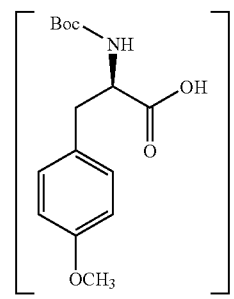

(4.9 g, 16.5 mmol), EDC (4.3 g, 22.5 mmol), HOBT (3.0 g, 22.5 mmol), DMAP (0.2 g, 0. 15 mmol) in CH$_2$Cl$_2$, and DMF (1:1, 50 mL) were added Et$_3$N (10.5 mL, 75.0 mmol) and 4-butanoyl-4-phenyl-piperdine hydrogen chloride

(4.0 g, 15.0 mmol), sequentially. The reaction mixture was stirred at RT overnight. The reaction mixture was diluted with EtOAc (200 mL) and washed with HCl (1 N, 200 mL), water (200 mL), NaOH (0.5 N, 200 mL), and water (200 mL). The organic layer was dried over anhydrous Na$_2$SO$_4$, and the solvent was subsequently removed under reduced pressure. The resulting material was >90% pure as judged by HPLC and used without further purification.

Step B:

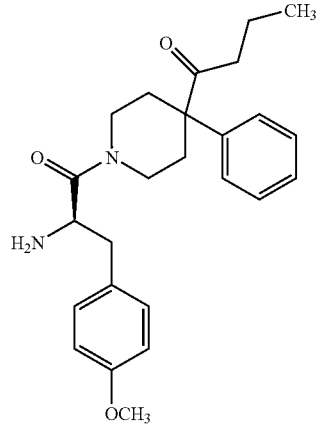

(1B)

To a solution of compound 1A (12.0 mmol) in wet CH$_2$Cl$_2$ (30 mL plus 2 mL water) was added TFA (15 mL). The solution was stirred at RT for 1 h before removing the solvents. The residue was dissolved in EtOAc (300 mL) and washed with water (200 mL), NaOH (0.5 N, 200 mL), and water (200 mL). The organic layer was dried over anhydrous Na₂SO₄, and the solvent removed under reduced pressure. The resulting material (compound 1B) was >90% pure as judged by HPLC and used without further purification.

Step C:

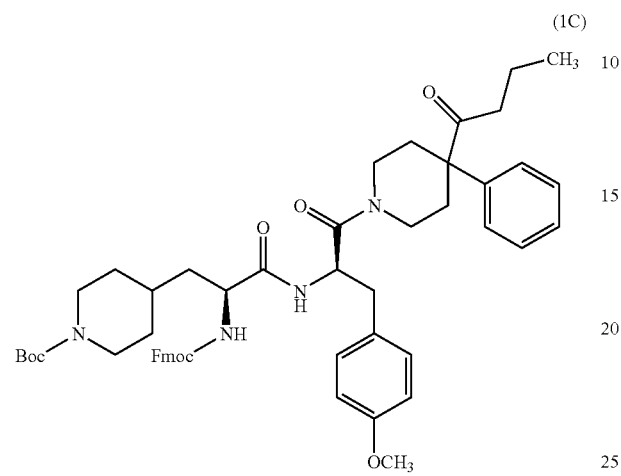

(1C)

To a solution of Nα-Fmoc-3-(4-N-Boc-piperidine)-L-alanine (0.33 g, 0.67 mmol), EDC (0.18 g, 0.92 mmol), HOBT (0.09 g, 0.92 mmol), DMAP (catalytic) in CH₂Cl₂, and DMF (1:1, 50 mL) were added Et₃N (0.25 mL, 1.8 mmol) and compound 1B (0.25 g, 0.61 mmol), sequentially. The reaction mixture was stirred at RT overnight. The reaction mixture was diluted with EtOAc (200 mL) and washed with HCl (1 N, 200 mL), water (200 mL), NaOH (0.5 N, 200 mL), and water (200 mL). The organic layer was dried over anhydrous Na₂SO₄, and the solvent was subsequently removed under reduced pressure to provide compound 1C.

Step D:

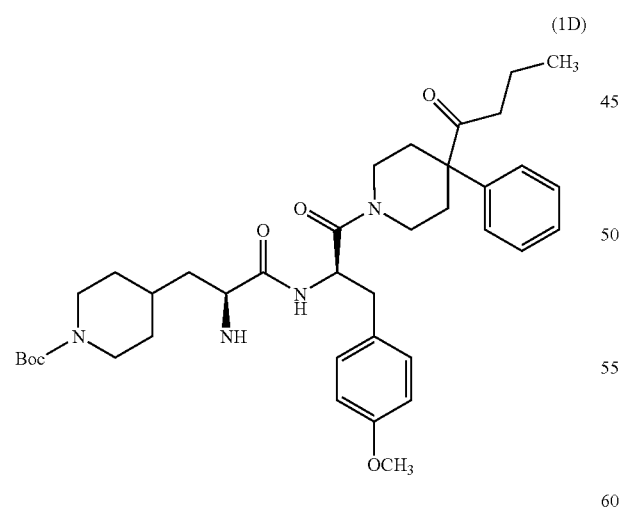

(1D)

Compound 1C was treated with diethylamine in CH₂Cl₂ (20%) followed by evaporation, to provide compound 1D.

Step E:

Compound 1D was treated with TFA as described in Step B. Example 1 was obtained which was purified by preparative HPLC with a purity of 89% as judged by HPLC.

EXAMPLE 2

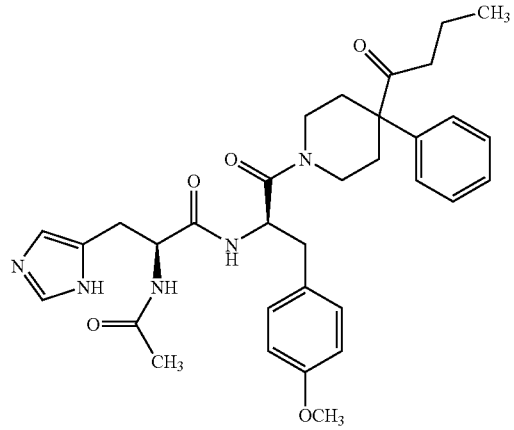

Step A:

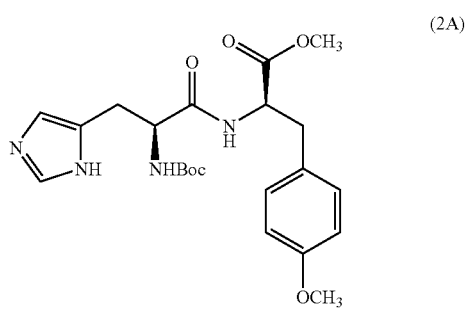

(2A)

To a solution of N-Boc-L-histidine

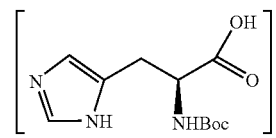

(3.1 g, 12.7 mmols), EDC (3.6 g, 19.1 mmols), HOBT (2.6 g, 19.1 mmols), DMAP (0.16 g, 1.3 mmols) in CH₂Cl₂, and DMF (1:1, 50 mL) were added Et₃N (8.8 mL, 64.0 mmols) and D-4-methoxyphenylalanine methyl ester hydrochloride

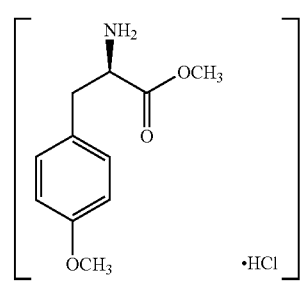

(2.9 g, 12.0 mmol), sequentially. The reaction mixture was stirred at RT overnight. The reaction mixture was diluted with EtOAc (200 mL) and washed with water (200 mL), NaOH (0.5 N, 200 mL), and water (200 mL). The organic layer was dried over anhydrous Na₂SO₄, and the solvent was subsequently removed under reduced pressure. The resulting compound 1A was >90% pure as judged by HPLC and used without further purification in Step B.

Step B:

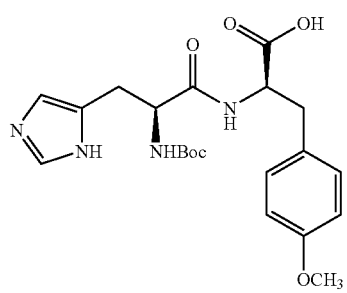
(2B)

To a solution of Compound 2A (12.0 mmol) in CH₃OH (13 mL) was added NaOH (2N, 13 mL) to make the final concentration of NaOH ~1 N. This solution was stirred at RT for 2 h before being diluted with water (100 mL). The aqueous layer was extracted with Et₂O (100 mL×2), and the organic matter was discarded. The aqueous layer was acidified with HCl (6 N) to pH ~2, and extracted with EtOAc (100 mL×2). The combined organic layers were dried over anhydrous Na₂SO₄, and the solvent was subsequently removed under reduced pressure. The resulting Compound 2B was a white solid with a purity >90% as judged by HPLC. This intermediate was used without further purification for Step C.

Step C:

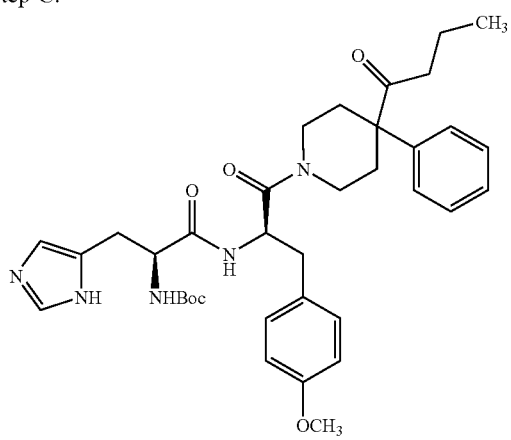
(2C)

To a solution of Compound 2B (0.5 g, 1.1 mmols), EDC (0.3 g g, 1.6 mmols), HOBT (0.22 g, 1.6 mmols), and DMAP (0.13 g, 1.1 mmols) in CH₂Cl₂ (25 mL) were added Et₃N (0.8 mL, 5.5 mmols) and 4-butyryl-4-phenyl-piperidine hydrochloride (0.35 g, 1.3 mmols), sequentially. The reaction mixture was stirred at RT overnight. The reaction mixture was diluted with EtOAc (100 mL) and washed with HCl (0.5 N, 100 mL), water (100 mL), NaOH (0.5 N, 100 mL), and water (100 mL). The organic layer was dried over anhydrous Na₂SO₄, and the solvent removed under reduced pressure. The resulting Compound 1C was >90% pure as judged by HPLC and used without further purification in Step D.

Step D:

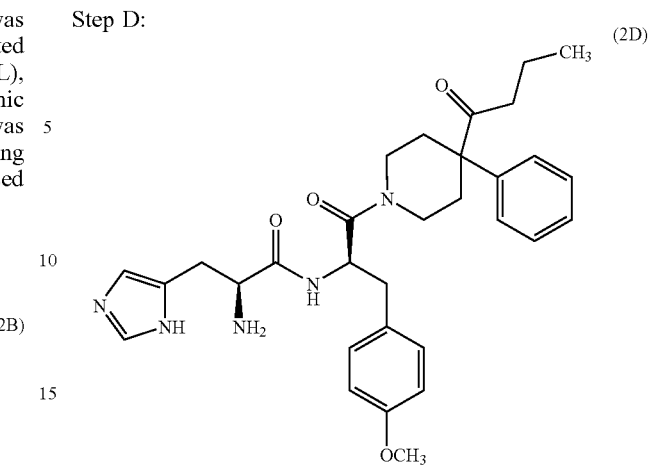
(2D)

To a solution of the Boc-protected Compound 2C (1.1 mmols) in wet CH₂Cl₂ (20 mL plus 1 mL water) was added TFA (10 mL). The solution was stirred at RT for 1 h before the solvents were removed. The crude reaction mixture was purified by preparative HPLC to obtain compound 2D at >95% purity as judged by HPLC. HPLC (min)=2.5, MS (M+H)⁺=546.4.

Step E:

To a solution of compound 2D (0.1 g, 0.18 mmol) in CH₂Cl₂ (10 mL) was added Et₃N (0.075 mL, 0.54 mmol). This solution was cooled to 0° C., and then acetyl chloride was added (0.02 g, 0.27 mmol). The reaction mixture was stirred at RT until all the amine was consumed. The reaction mixture was diluted with EtOAc (100 mL) and washed with HCl (0.5 N, 100 mL), water (100 mL), NaOH (0.5 N, 100 mL), and water (100 mL). The organic layer was dried over anhydrous Na₂SO₄, and the solvent removed under reduced pressure to provide Example 2 which was purified by preparative HPLC. Purity=94%, HPLC ret. time (min.)= 2.71, MS (M+H)⁺=588.

EXAMPLES 3–43

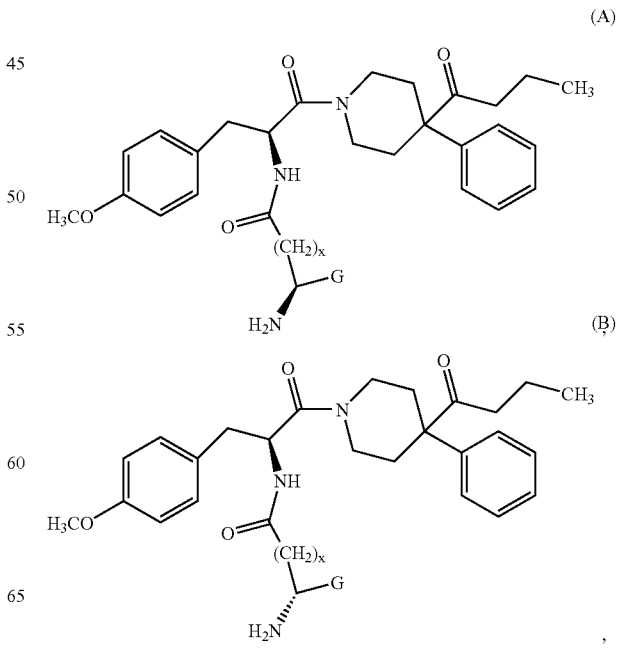

Compounds of the above formulae (A) and (B), wherein the groups G and x have the values listed in Table 1, were prepared following the procedure described above for Example 2:
TABLE 1
| Ex. | Core | x | G | Purity (%) | HPLC RT (min) | Mass (M + H) |
|---|---|---|---|---|---|---|
| 3 | B | 0 | 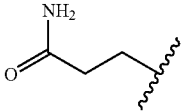 | 87 | 2.6 | 537.21 |
| 4 | B | 0 | 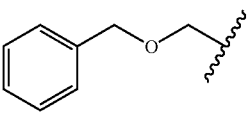 | 80 | 3.6 | 586.5 |
| 5 | A | 0 | 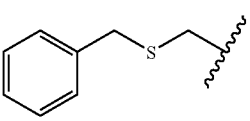 | 83 | 3.7 | 602.46 |
| 6 | A | 0 | 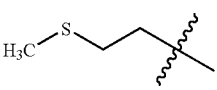 | 78 | 3.4 | 540.43 |
| 7 | A | 0 | 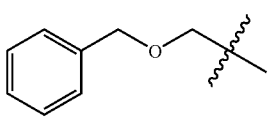 | 85 | 3.1 | 586.23 |
| 8 | B | 0 | 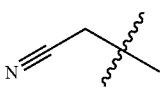 | 93 | 3.0 | 505.35 |
| 9 | B | 1 | 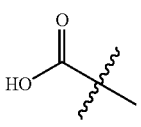 | 85 | 2.7 | 524.22 |
| 10 | B | 2 | 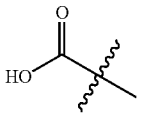 | 84 | 2.7 | 538.24 |
| 11 | B | 2 | 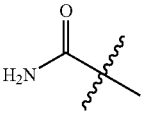 | 100 | 2.7 | 537.28 |
| 12 | B | 0 | 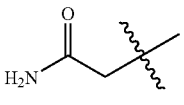 | 92 | 2.6 | 523.17 |
| 13 | A | 0 | 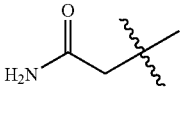 | 93 | 2.6 | 523.35 |

TABLE 1-continued

| Ex. | Core | x | G | Purity (%) | HPLC RT (min) | Mass (M + H) |
|---|---|---|---|---|---|---|
| 14 | A | 0 | 4-methoxybenzyl-S-CH< | 78 | 3.1 | 632.18 |
| 15 | A | 0 | cyclohexyl-O-C(O)-CH2CH2-C< | 83 | 3.3 | 620.37 |
| 16 | A | 0 | benzyl-O-CH(CH3)-C< | 95 | 3.1 | 600.24 |
| 17 | A | 0 | H3C-S-CH2-C< | 94 | 2.8 | 526.05 |
| 18 | A | 0 | cyclohexyl-O-C(O)-CH2CH2-C< | 78 | 3.2 | 620.26 |
| 19 | A | 0 | H3C-O-C(O)-CH2-C< | 96 | 2.7 | 538.23 |
| 20 | A | 2 | HO-C(O)-C< | 81 | 2.7 | 538.14 |
| 21 | A | 0 | (S)-pyrrolidin-2-yl-CH2-C< | 91 | 2.5 | 549 |
| 22 | B | 0 | (S)-pyrrolidin-2-yl-CH2-C< | 86 | 2.56 | 549.31 |
| 23 | A | 0 | piperidin-4-yl-C< | 88 | 2.49 | 549.3 |
| 24 | B | 0 | piperidin-4-yl-C< | 91 | 2.52 | 549.31 |

TABLE 1-continued

| Ex. | Core | x | G | Purity (%) | HPLC RT (min) | Mass (M + H) |
|---|---|---|---|---|---|---|
| 25 | B | 0 | (4-piperidinylmethyl) | 89 | 2.53 | 563.42 |
| 26 | A | 0 | (ureidobutyl) | 78 | 2.62 | 566.29 |
| 27 | B | 0 | (ureidobutyl) | 83 | 2.67 | 566.31 |
| 28 | B | 0 | (carbamoylpropyl) | 87 | 2.6 | 537.21 |
| 29 | B | 0 | (benzyloxymethyl) | 80 | 3.6 | 586.5 |
| 30 | A | 0 | (benzylthiomethyl) | 83 | 3.7 | 602.46 |
| 31 | A | 0 | (methylthioethyl) | 78 | 3.4 | 540.43 |
| 32 | A | 0 | (benzyloxymethyl) | 85 | 3.1 | 586.23 |
| 33 | B | 0 | (cyanomethyl) | 93 | 3.0 | 505.35 |
| 34 | B | 0 | (carbamoylmethyl) | 92 | 2.6 | 523.17 |
| 35 | A | 0 | (carbamoylmethyl) | 93 | 2.6 | 523.35 |
| 36 | A | 0 | (4-methoxybenzylthioethyl) | 78 | 3.1 | 632.18 |

TABLE 1-continued
| Ex. | Core | x | G | Purity (%) | HPLC RT (min) | Mass (M + H) |
|---|---|---|---|---|---|---|
| 37 | A | 0 | 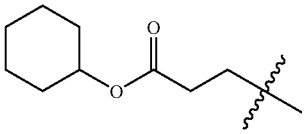 | 83 | 3.3 | 620.37 |
| 38 | A | 0 | 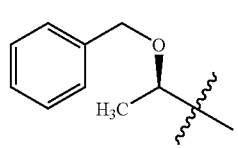 | 95 | 3.1 | 600.24 |
| 39 | A | 0 | 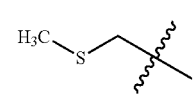 | 94 | 2.8 | 526.05 |
| 40 | A | 0 | 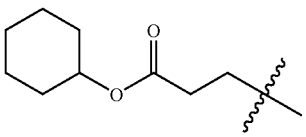 | 78 | 3.2 | 620.26 |
| 41 | A | 0 | 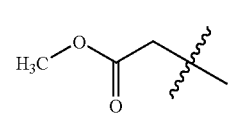 | 96 | 2.7 | 538.23 |
| 42 | A | 0 | 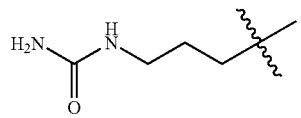 | 78 | 2.62 | 566.29 |
| 43 | B | 0 | 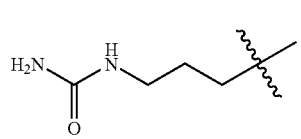 | 83 | 2.67 | 566.31 |

EXAMPLES 44–48
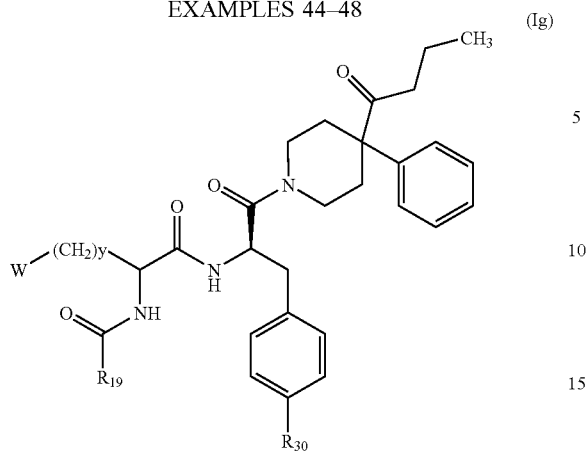
(Ig)
Compounds having the above formula (Ig), wherein W, y and $R_{15}$ have the values Table 2, were prepared following the same or similar procedure as described or Example 2.
TABLE 2
| Ex. | W | y | $R_{19}$ | $R_{30}$ | Purity (%) | HPLC Ret time (min) | MS (M + H) |
|---|---|---|---|---|---|---|---|
| 44 | imidazole | 1 | —CH$_3$ | —OCH$_3$ | 94 | 2.71 | 588 |
| 45 | imidazole | 1 | phenyl | —OCH$_3$ | 96 | 2.97 | 650.27 |
| 46 | imidazole | 1 | —CH$_3$ | Cl | 96 | — | 593 |
| 47 | imidazole | 1 | phenyl | Cl | 90 | — | 655 |
| 48 | NH$_2$ | 3 | —CH$_3$ | —OCH$_3$ | 80 | 2.67 | 565.29 |
EXAMPLES 49–84
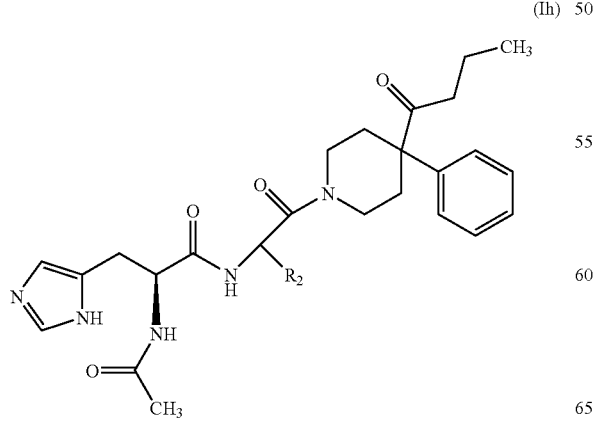
(Ih)

Compounds of formula (Ih), above, wherein $R_2$ has the values listed in Table 3, were prepared following the same or similar procedure as described above for Example 2.

TABLE 3

| Ex. No. | $R_2$ | Purity (%) | HPLC RT (min) | Mass (M + H) |
|---|---|---|---|---|
| 49 | -CH₂CH(CH₃)₂ (isobutyl) | 79 | 3.2 | 524.39 |
| 50 | -(CH₂)₃CH₃ (n-butyl) | 84 | 3.3 | 524.39 |
| 51 | -CH₂-(2-thienyl) | 80 | 3.2 | 564.28 |
| 52 | -CH₂-(4-nitrophenyl) | 81 | 3.1 | 603.34 |
| 53 | -CH₂-(2-naphthyl) | 93 | 3.5 | 608.37 |
| 54 | -CH₂CH₂-phenyl | 84 | 3.4 | 572.34 |
| 55 | -CH₂-(1-naphthyl) | 86 | 3.5 | 608.37 |
| 56 | -CH₂-(4-fluorophenyl) | 85 | 3.3 | 576.31 |
| 57 | -CH₂-(4-iodophenyl) | 96 | 3.5 | 684.22 |
| 58 | -CH₂-(benzothienyl) | 72 | 3.5 | 614.34 |

TABLE 3-continued
| Ex. No. | R₂ | Purity (%) | HPLC RT (min) | Mass (M + H) |
|---|---|---|---|---|
| 59 | 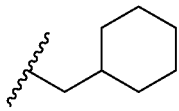 | 88 | 3.6 | 564.37 |
| 60 | 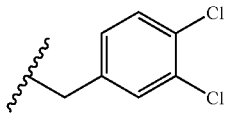 | 85 | 3.6 | 626.27 |
| 61 | 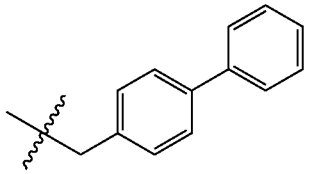 | 92 | 3.7 | 634.38 |
| 62 | 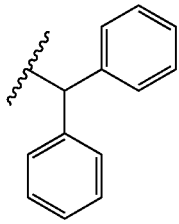 | 91 | 3.5 | 634.38 |
| 63 | 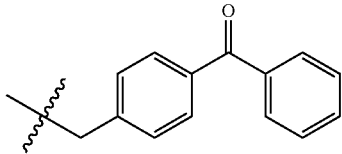 | 71 | 3.4 | 662.34 |
| 64 | 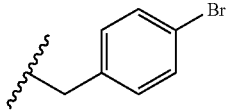 | 92 | 3.5 | 636.26 |
| 65 | 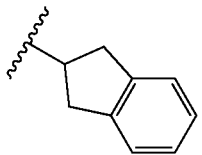 | 87 | 3.4 | 584.35 |
| 66 | 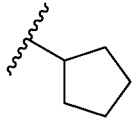 | 84 | 3.3 | 536.38 |
| 67 | 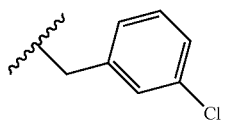 | 86 | 3.4 | 592.32 |

TABLE 3-continued

| Ex. No. | R2 | Purity (%) | HPLC RT (min) | Mass (M + H) |
|---|---|---|---|---|
| 68 | 3,4-difluorobenzyl | 84 | 3.3 | 594.33 |
| 69 | 2-fluorobenzyl | 83 | 3.3 | 576.31 |
| 70 | 3-fluorobenzyl | 84 | 3.3 | 576.31 |
| 71 | 3,5-difluorobenzyl | 80 | 3.4 | 594.31 |
| 72 | 2-chlorobenzyl | 89 | 3.4 | 592.31 |
| 73 | 4-(allyloxy)benzyl | 78 | 3.5 | 614.39 |
| 74 | pyridin-3-ylmethyl | 83 | 2.5 | 559.32 |
| 75 | thiazol-4-ylmethyl | 82 | 2.9 | 565.27 |
| 76 | pyridin-4-ylmethyl | 82 | 2.5 | 559.31 |
| 77 | 3-cyanobenzyl | 79 | 3.0 | 583.32 |
| 78 | H | 81 | 2.7 | 468.29 |
| 79 | —CH$_3$ | 84 | 2.8 | 482.31 |
| 80 | 4-cyanobenzyl | 85 | 3.0 | 583.33 |

TABLE 3-continued

| Ex. No. | R₂ | Purity (%) | HPLC RT (min) | Mass (M + H) |
|---|---|---|---|---|
| 81 | (4-methylbenzyl) | 80 | 3.4 | 572.33 |
| 82 | (cinnamyl) | 75 | 3.4 | 584.33 |
| 83 | (3,4-dimethoxybenzyl) | 88 | 3.0 | 618.37 |
| 84 | (2-cyclohexylethyl) | 86 | 3.8 | 578.38 |

EXAMPLES 85–93

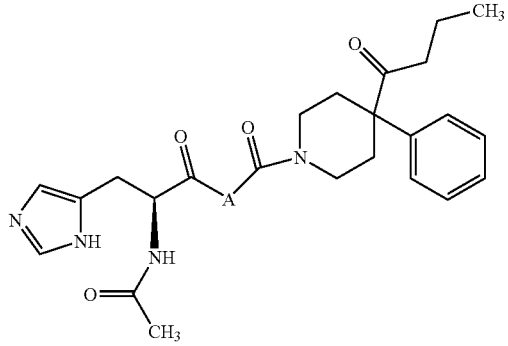

(Ii)

Compounds of formula (Ii), above, wherein A has the values listed in Table 4, were following the same or similar procedure as described above for Example 2.

TABLE 4

| Ex. No. | A | Purity (%) | HPLC ret. t. = (min) | Mass (M + H) |
|---|---|---|---|---|
| 85 | —CH₂CH₂— | 76 | 2.7 | 482.32 |
| 86 | (tetrahydroisoquinoline) | 71 | 3.2 | 570.32 |
| 87 | (NH-phenyl) | 80 | 3.1 | 530.32 |
| 88 | (piperidine) | 73 | 3.0 | 522.38 |

TABLE 4-continued
| Ex. No. | A | Purity (%) | HPLC ret. t. = (min) | Mass (M + H) |
|---|---|---|---|---|
| 89 | | 87 | 2.9 | 522.38 |
| 90 | | 76 | 3.3 | 586.36 |
| 91 | | 80 | 3.2 | 584.34 |
| 92 | | 71 | 3.4 | 584.33 |
| 93 | | 83 | 3.4 | 584.35 |
EXAMPLES 94–145
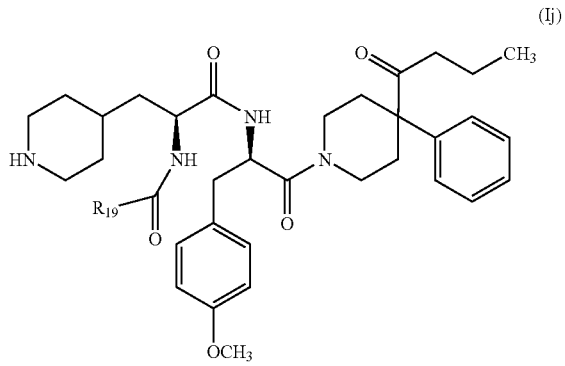
(Ij)
Compounds having the above formula (Ij), wherein $R_{19}$ has the values listed in Table 5, were prepared following the same or similar procedure as described above for Examples 1 and 2.
TABLE 5
| Ex. No. | $R_{19}$ | Purity (%) | HPLC RT (min) | Mass (M + H) |
|---|---|---|---|---|
| 94 | | 84 | 3.59 | 729.4 |
| 95 | | 90 | 2.84 | 695.9 |
| 96 | | 80 | 3.72 | 743 |
| 97 | | 88 | 3.43 | 710.9 |
| 98 | | 81 | 3.37 | 680.9 |
| 99 | | 80 | 3.21 | 690.9 |

TABLE 5-continued

| Ex. No. | R₁₉ | Purity (%) | HPLC RT (min) | Mass (M + H) |
|---|---|---|---|---|
| 100 | phenoxyacetyl | 82 | 3.43 | 696.9 |
| 101 | 2-chlorophenyl | 84 | 3.53 | 701.3 |
| 102 | pyridin-3-yl | 85 | 3.02 | 667.9 |
| 103 | pyridin-4-yl | 84 | 2.97 | 667.9 |
| 104 | benzyloxyacetyl | 85 | 3.49 | 710.9 |
| 105 | 4-nitrophenyl | 85 | 3.41 | 711.9 |
| 106 | biphenyl-4-yl | 81 | 3.7 | 743 |
| 107 | 3-(3-methoxyphenyl)propyl | 76 | 3.46 | 724.9 |
| 108 | 3-(4-chlorophenyl)propyl | 85 | 3.61 | 729.4 |
| 109 | 4-phenylbutyl | 75 | 3.58 | 708.9 |
| 110 | cyclohexylmethyl | 75 | 3.61 | 686.9 |
| 111 | quinolin-3-yl | 80 | 3.27 | 717.9 |
| 112 | 2-phenoxyphenyl | 80 | 3.6 | 759 |
| 113 | 3-phenoxyphenyl | 81 | 3.72 | 759 |
| 114 | cyclopentylmethyl | 75 | 3.52 | 672.9 |
| 115 | Me | 90 | 3.08 | 604.8 |
| 116 | 4-phenoxyphenyl | 75 | 3.73 | 759 |
| 117 | Et | 75 | 3.16 | 618.8 |
| 118 | 1H-imidazol-5-yl | 85 | 2.89 | 656.8 |
| 119 | cyclopropyl | 75 | 3.2 | 630.8 |
| 120 | 3-(dimethylamino)phenyl | 75 | 3.12 | 709.9 |
| 121 | n-propyl | 80 | 3.24 | 632.9 |
| 122 | sec-butyl | 90 | 3.36 | 646.9 |

TABLE 5-continued
| Ex. No. | R19 | Purity (%) | HPLC RT (min) | Mass (M + H) |
|---|---|---|---|---|
| 123 | 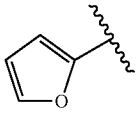 | 78 | 3.2 | 656.8 |
| 124 | 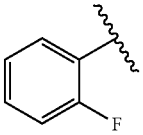 | 90 | 3.32 | 684.9 |
| 125 | 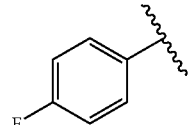 | 73 | 3.4 | 684.9 |
| 126 | 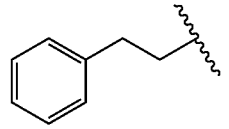 | 79 | 3.45 | 694.9 |
| 127 | 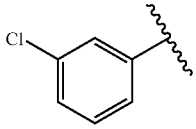 | 75 | 3.35 | 701.3 |
| 128 | 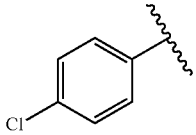 | 80 | 3.54 | 701.3 |
| 129 | 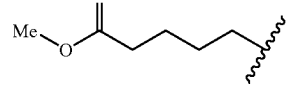 | 75 | 3.27 | 704.9 |
| 130 | 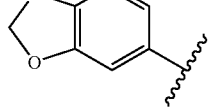 | 81 | 3.33 | 710.9 |
| 131 | 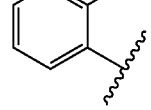 | 75 | 3.25 | 711.9 |
| 132 | 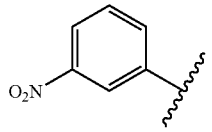 | 88 | 3.39 | 711.9 |
TABLE 5-continued
| Ex. No. | R19 | Purity (%) | HPLC RT (min) | Mass (M + H) |
|---|---|---|---|---|
| 133 | 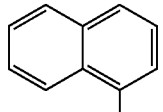 | 84 | 3.5 | 716.9 |
| 134 |  | 80 | 3.25 | 632.9 |
| 135 | 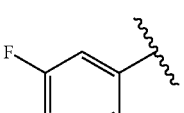 | 80 | 3.41 | 684.9 |
| 136 | 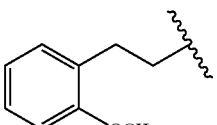 | 77 | 3.51 | 724.9 |
| 137 | 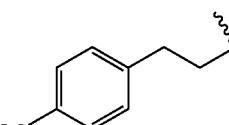 | 80 | 3.43 | 724.9 |
| 138 | 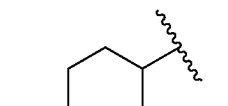 | 75 | 3.51 | 672.9 |
| 139 | 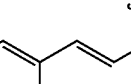 | 80 | 3.49 | 692.9 |
| 140 | 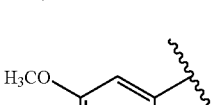 | 75 | 3.39 | 696.9 |
| 141 | 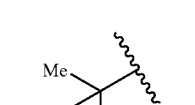 | 90 | 3.36 | 646.9 |
| 142 | 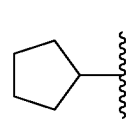 | 90 | 3.41 | 658.9 |

TABLE 5-continued

| Ex. No. | R19 | Purity (%) | HPLC RT (min) | Mass (M + H) |
|---|---|---|---|---|
| 143 | 2-(NMe2)-C6H4-CH2- | 90 | 2.96 | 709.9 |
| 144 | 2-OCH3-C6H4-CH2- | 80 | 3.35 | 696.9 |
| 145 | 4-OCH3-C6H4-CH2- | 90 | 3.36 | 696.9 |

EXAMPLES 146–200

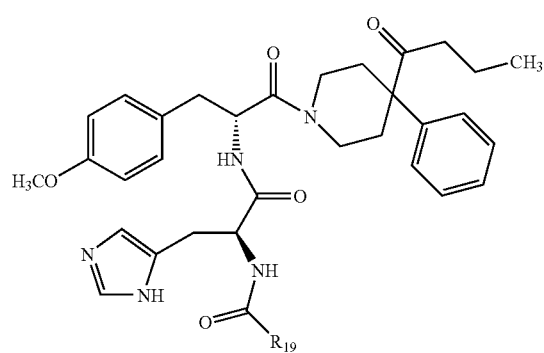

(Ik)

Compounds having the above formula (Ik), wherein R19 has the values listed in Table 6, were prepared following the same or similar procedure as for Example 1.

TABLE 6

| Ex. No. | R19 | Purity (%) | HPLC RT (min) | Mass (M + H) |
|---|---|---|---|---|
| 146 | cyclopentyl- | 80 | 3.36 | 642.4 |
| 147 | 2-Cl-C6H4-CH2CH2- | 70 | 3.56 | 712.3 |
| 148 | cyclopentyl-CH2- | 75 | 3.47 | 656.4 |
| 149 | pyridin-3-yl-CH2CH2- | 76.5 | 2.83 | 679.3 |
| 150 | 4-PhO-C6H4- | 75.7 | 3.69 | 742.3 |
| 151 | biphenyl-3-yl- | 75.1 | 3.68 | 726.4 |
| 152 | cyclopropyl- | 80 | 3.18 | 614.4 |
| 153 | 3-(NMe2)-C6H4- | 72.6 | 3.11 | 693.4 |
| 154 | Me-CH2CH2- | 75 | 3.23 | 616.4 |
| 155 | Me2CH-CH2- | 80 | 3.31 | 630.4 |
| 156 | 2-OCH3-C6H4-CH2- | 72 | 3.39 | 694.4 |
| 157 | Me-CH2CH2CH2- | 75 | 3.33 | 630.4 |
| 158 | furan-2-yl- | 90 | 3.16 | 640.4 |

TABLE 6-continued
| Ex. No. | R19 | Purity (%) | HPLC RT (min) | Mass (M + H) |
|---|---|---|---|---|
| 159 | 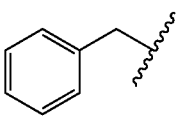 | 85 | 3.32 | 664.4 |
| 160 | 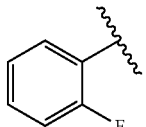 | 80.4 | 3.28 | 668.3 |
| 161 | 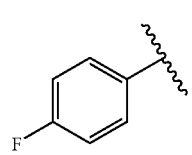 | 78.2 | 3.36 | 668.3 |
| 162 | 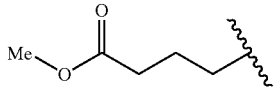 | 70 | 3.17 | 674.4 |
| 163 | 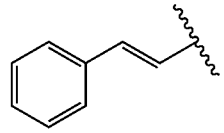 | 75 | 3.45 | 676.4 |
| 164 | 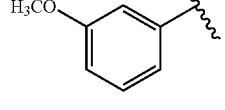 | 75 | 3.36 | 680.3 |
| 165 | 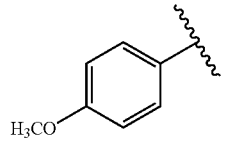 | 75 | 3.33 | 680.3 |
| 166 | 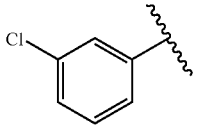 | 75.3 | 3.49 | 684.3 |
| 167 | 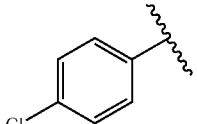 | 76.1 | 3.5 | 684.3 |
| 168 | 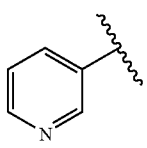 | 80 | 3.01 | 651.3 |
| 169 | 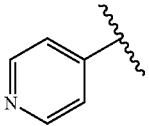 | 85 | 2.96 | 651.3 |
| 170 |  | 70 | 3.24 | 688.4 |
| 171 | 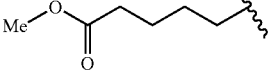 | 79.4 | 3.3 | 694.3 |
| 172 | 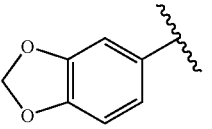 | 82.9 | 3.34 | 695.3 |
| 173 | 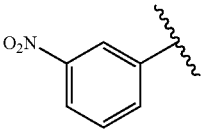 | 83.7 | 3.37 | 695.3 |
| 174 | 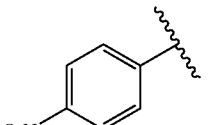 | 75 | 3.66 | 726.4 |
| 175 | 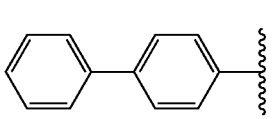 | 75 | 3.31 | 630.4 |
| 176 | 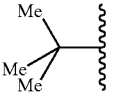 | 70 | 3.21 | 616.4 |
| 177 | 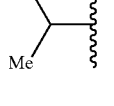 | 79.6 | 3.36 | 668.3 |
| 178 | 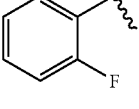 | 85 | 3.52 | 706.3 |
| 179 | 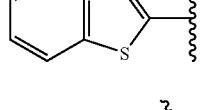 | 70 | 3.47 | 708.4 |

TABLE 6-continued

| Ex. No. | R$_{19}$ | Purity (%) | HPLC RT (min) | Mass (M + H) |
|---|---|---|---|---|
| 180 | 4-methoxyphenylpropyl | 70 | 3.42 | 708.4 |
| 181 | 3-methoxyphenylpropyl | 70 | 3.43 | 708.4 |
| 182 | 4-chlorophenylpropyl | 70 | 3.59 | 712.4 |
| 183 | phenylbutyl | 75.5 | 3.54 | 692.4 |
| 184 | cyclohexyl | 75 | 3.46 | 656.4 |
| 185 | cyclohexylmethyl | 72 | 3.56 | 670.4 |
| 186 | quinolin-3-yl | 72 | 3.25 | 701.4 |
| 187 | 3-phenoxyphenyl | 76.3 | 3.68 | 742.4 |
| 188 | 2-(dimethylamino)phenyl | 90 | 2.95 | 693.4 |
| 189 | 2-methoxyphenyl | 90 | 3.32 | 680.3 |
| 190 | 2-nitrophenyl | 90 | 4.33 | 695.3 |
| 191 | 2-phenoxyphenyl | 90 | 3.57 | 742.3 |
| 192 | ethyl | 90 | 3.13 | 602.3 |
| 193 | 2-chlorophenyl | 90 | 3.29 | 684.3 |
| 194 | benzyloxymethyl | 90 | 3.44 | 694.3 |
| 195 | naphthalen-1-yl | 92 | 3.45 | 700.4 |
| 196 | furan-2-ylmethyl | 90 | 3.26 | 670.3 |
| 197 | biphenyl-2-yl | 90 | 3.53 | 726.3 |

TABLE 6-continued

| Ex. No. | R_{19} | Purity (%) | HPLC RT (min) | Mass (M + H) |
|---|---|---|---|---|
| 198 | imidazole | 90 | 4.33 | 640.3 |
| 199 | 4-(dimethylamino)phenyl | 90 | 3.33 | 693.4 |
| 200 | phenoxymethyl | 90 | 3.37 | 680.3 |

EXAMPLES 201–215

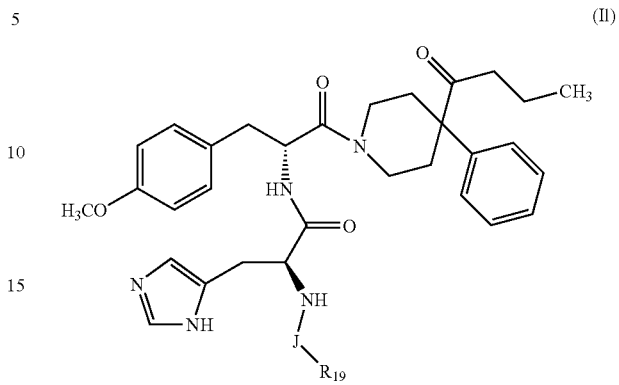

(II)

Compounds having the above formula (II), wherein J and $R_{19}$ have the values listed in Table 7, were prepared following the same or similar procedure as for Example 1. For examples 201–205 and 213–215, in the last step, compound 2D was dissolved in DCM and reacted with 1.2 eq of the appropriate sulfonyl chloride or chloroformate in presence of 3 eq of resin bound morpholine (Argonaut Technologies) at RT overnight. After filtration and concentration the residue was purified by RP-prep HPLC. For examples 206–212, in the last step compound 2D was reacted with 1.1 eq of the appropriate isocyanate in toluene at RT overnight. After concentration, the residue was purified by RP-prep HPLC.

TABLE 7

| Ex. No. | J | $R_{19}$ | Purity (%) | HPLC RT (min) | Mass (M + H) |
|---|---|---|---|---|---|
| 201 | —SO_2— | —CH_3 | 86 | 3.03 | 623.8 |
| 202 | —SO_2— | —CH_2CH_3 | 80 | 3.10 | 637.8 |
| 203 | —SO_2— | —CH_2CH_2CH_3 | 95 | 3.20 | 651.8 |
| 204 | —SO_2— | phenyl | 95 | 3.22 | 685.8 |
| 205 | —SO_2— | benzyl | 95 | 3.32 | 699.9 |
| 206 | —C(=O)NH— | —CH_2CH_3 | 92 | 3.12 | 616.8 |
| 207 | —C(=O)NH— | —CH_3 | 80 | 3.05 | 602.7 |
| 208 | —C(=O)NH— | —CH(CH_3)(CH_3) | 95 | 3.22 | 630.8 |
| 209 | —C(=O)NH— | —CH_2CH_2CH_3 | 95 | 3.23 | 630.8 |
| 210 | —C(=O)NH— | phenyl | 95 | 3.36 | 664.8 |

TABLE 7-continued

| Ex. No. | J | $R_{19}$ | Purity (%) | HPLC RT (min) | Mass (M + H) |
|---|---|---|---|---|---|
| 211 | —C(=O)NH— | 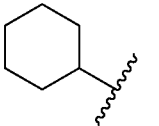 | 95 | 3.46 | 670.9 |
| 212 | —C(=O)NH— | 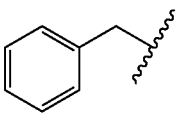 | 95 | 3.36 | 678.8 |
| 213 | —CO$_2$— | —CH$_2$CH$_2$CH$_3$ | 94 | 3.69 | 631.8 |
| 214 | —CO$_2$— | —CH$_3$ | 91 | 3.47 | 603.7 |
| 215 | —CO$_2$— | —CH$_2$CH$_3$ | 90 | 3.56 | 617.8 |

EXAMPLE 216

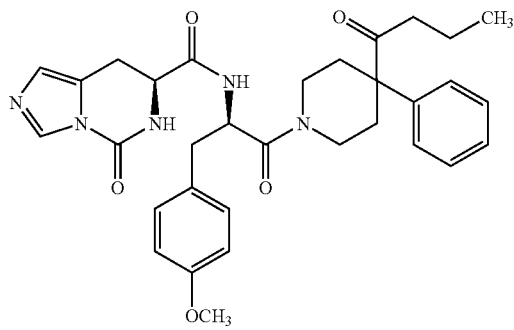

Example 216 was prepared following the same or similar procedure as described above for Example 2. In the last step, 2D was reacted with 1.2eq of phenylchloroformate in DCM in presence of 3 eq of resin bound morpholine. After filtration and concentration, the residue was purified by RP-prep HPLC. Purity=98%, HPLC ret. time (min)=3.42, MS (M+H)$^+$=572.

EXAMPLES 217–311

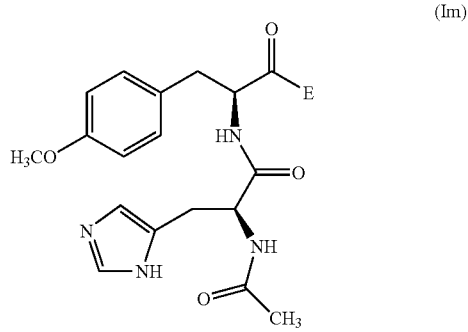

(Im)

Compounds having the above formula (Im), wherein E has the values listed in Table 8, were prepared following the same or similar procedure as for Example 1.

TABLE 8

| Ex. No. | E | Purity (%) | HPLC RT (min) | Mass (M + H) |
|---|---|---|---|---|
| 217 | 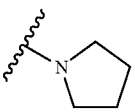 | 88.9% | 2.2 | 427.5 |
| 218 | 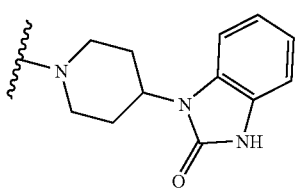 | 87.4% | 2.6 | 573.7 |

TABLE 8-continued

| Ex. No. | E | Purity (%) | HPLC RT (min) | Mass (M + H) |
|---|---|---|---|---|
| 219 | (1-phenyl-4-oxo-1,3,8-triazaspiro[4.5]decan-8-yl) | 74.0% | 2.6 | 587.7 |
| 220 | (piperidin-1-yl) | 92.7% | 2.4 | 441.5 |
| 221 | (4-hydroxy-4-phenylpiperidin-1-yl) | 78.6% | 2.6 | 533.6 |
| 222 | (4-phenylpiperidin-1-yl) | 80.6% | 3.0 | 517.6 |
| 223 | (4-methylpiperidin-1-yl) | 85.5% | 2.7 | 455.6 |
| 224 | (4-piperidin-1-yl-piperidin-1-yl) | 96.0% | 1.7 | 524.7 |
| 225 | (azepan-1-yl) | 88.4% | 2.6 | 455.6 |
| 226 | (decahydroisoquinolin-2-yl) | 80.8% | 3.1 | 495.6 |
| 227 | (4-pyrrolidin-1-yl-piperidin-1-yl) | 92.0% | 1.6 | 510.6 |

TABLE 8-continued

| Ex. No. | E | Purity (%) | HPLC RT (min) | Mass (M + H) |
|---|---|---|---|---|
| 228 | | 80.9% | 3.1 | 601.6 |
| 229 | | 85.4% | 2.7 | 588.7 |
| 230 | | 86.2% | 2.5 | 575.7 |
| 231 | | 88.3% | 3.2 | 531.7 |
| 232 | | 86.5% | 3.1 | 547.7 |
| 233 | | 85.4% | 3.2 | 618.1 |
| 234 | | 87.2% | 2.8 | 613.7 |
| 235 | | 92.3% | 3.3 | 565.7 |

TABLE 8-continued
| Ex. No. | E | Purity (%) | HPLC RT (min) | Mass (M + H) |
|---|---|---|---|---|
| 236 | 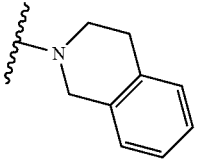 | 85.2% | 2.8 | 489.6 |
| 237 | 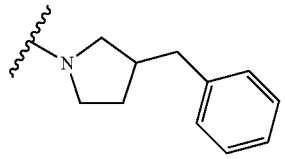 | 85.6% | 3.0 | 517.6 |
| 238 | 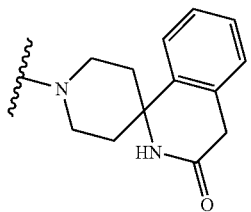 | 93.0% | 2.6 | 572.7 |
| 239 | 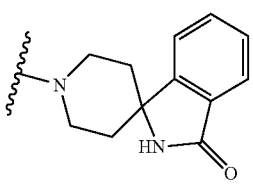 | 89.3% | 2.5 | 558.6 |
| 240 | 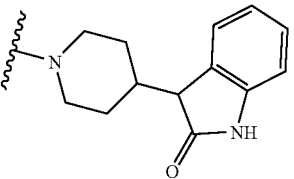 | 81.3% | 2.6 | 572.7 |
| 241 | 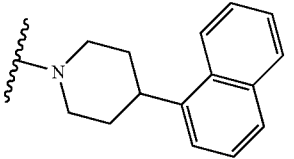 | 80.6% | 3.4 | 567.7 |
| 242 | 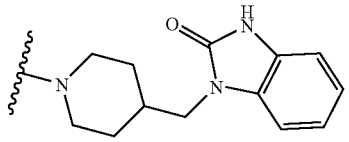 | 84.8% | 2.7 | 587.7 |
| 243 | 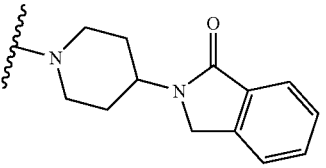 | 87.7% | 2.6 | 572.7 |

TABLE 8-continued
| Ex. No. | E | Purity (%) | HPLC RT (min) | Mass (M + H) |
|---|---|---|---|---|
| 244 | 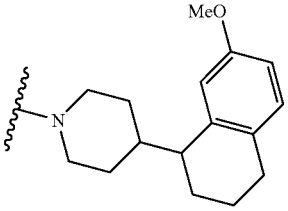 | 93.2% | 3.5 | 601.7 |
| 245 | 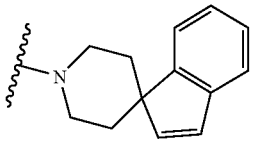 | 86.7% | 3.2 | 541.7 |
| 246 |  | 84.7% | 3.2 | 625.7 |
| 247 | 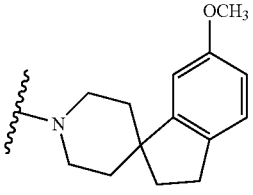 | 89.6% | 3.4 | 587.7 |
| 248 | 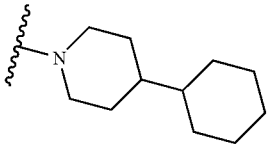 | 84.2% | 3.5 | 523.7 |
| 249 | 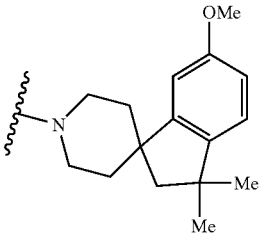 | 90.1% | 3.6 | 615.8 |
| 250 | 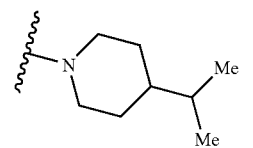 | 80.0% | 3.1 | 483.6 |
| 251 | 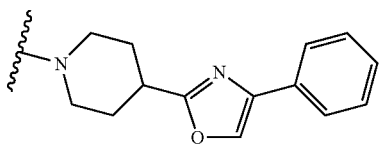 | 86.2% | 3.0 | 584.7 |

TABLE 8-continued

| Ex. No. | E | Purity (%) | HPLC RT (min) | Mass (M + H) |
|---|---|---|---|---|
| 252 | | 82.3% | 3.2 | 497.6 |
| 253 | | 71.0% | 2.6 | 587.7 |
| 254 | | 91.1% | 3.4 | 557.7 |
| 255 | | 82.6% | 2.7 | 577.7 |
| 256 | | 81.5% | 3.2 | 575.7 |
| 257 | | 80.4% | 1.8 | 521.6 |
| 258 | | 79.7% | 2.9 | 589.7 |
| 259 | | 93.0% | 2.0 | 574.7 |
| 260 | | 91.0% | 2.3 | 589.7 |

TABLE 8-continued
| Ex. No. | E | Purity (%) | HPLC RT (min) | Mass (M + H) |
|---|---|---|---|---|
| 261 | 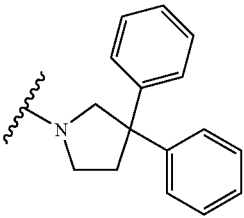 | 93.4% | 3.3 | 579.7 |
| 262 | 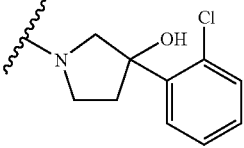 | 79.8% | 3.0 | 554.0 |
| 263 | 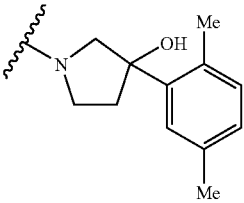 | 71.0% | 3.2 | 547.7 |
| 264 | 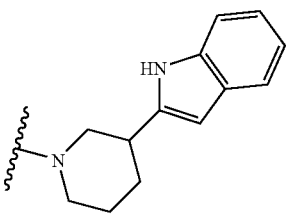 | 77.6% | 3.3 | 556.7 |
| 265 | 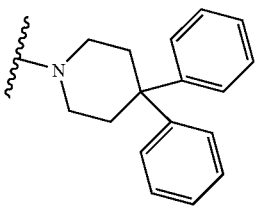 | 85.8% | 3.6 | 607.8 |
| 266 | 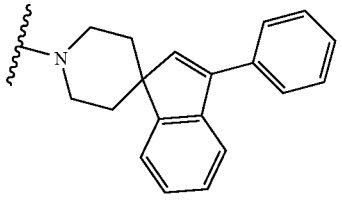 | 95.0% | 3.8 | 617.8 |
| 267 | 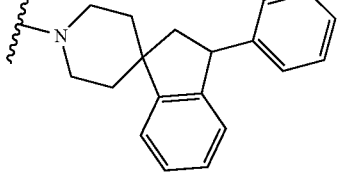 | 91.4% | 3.7 | 619.8 |

TABLE 8-continued
| Ex. No. | E | Purity (%) | HPLC RT (min) | Mass (M + H) |
|---|---|---|---|---|
| 268 | 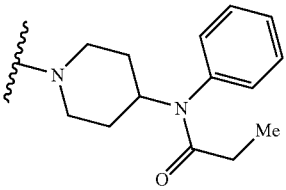 | 84.7% | 3.0 | 588.7 |
| 269 | 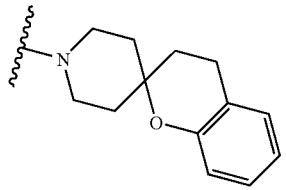 | 92.5% | 3.4 | 559.7 |
| 270 | 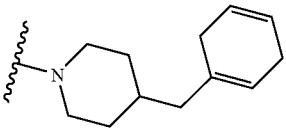 | 82.4% | 3.5 | 533.7 |
| 271 | 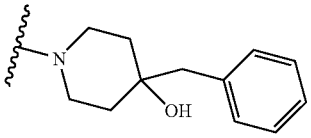 | 86.4% | 3.0 | 547.7 |
| 272 | 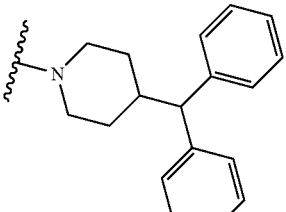 | 94.0% | 3.6 | 607.8 |
| 273 | 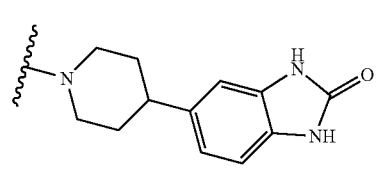 | 75.0% | 2.0 | 574.6 |
| 274 | 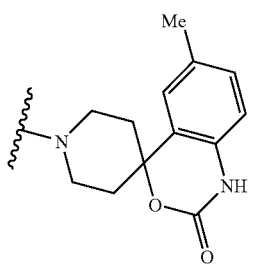 | 82.0% | 2.9 | 588.7 |

TABLE 8-continued

| Ex. No. | E | Purity (%) | HPLC RT (min) | Mass (M + H) |
|---|---|---|---|---|
| 275 | piperidine-cyclohexyl-CH2-triazole | 88.4% | 3.2 | 604.8 |
| 276 | NH-cyclobutyl | 86.0% | 2.3 | 427.5 |
| 277 | NH-cyclopentyl | 88.7% | 2.5 | 441.5 |
| 278 | NH-cyclohexyl | 88.7% | 2.7 | 455.6 |
| 279 | NH-(4-Me-cyclohexyl) | 88.7% | 3.0 | 469.6 |
| 280 | NH-CH(CH2OH)-CH2-Ph | 74.8% | 2.6 | 507.6 |
| 281 | NH-CH(Me)-CH2CH2-CH(Me)2 | 88.5% | 3.3 | 485.6 |
| 282 | NH-CH2-C(Me)3 | 81.2% | 2.6 | 443.5 |
| 283 | NH-CH2CH2-C(Me)3 | 86.0% | 2.9 | 457.6 |

TABLE 8-continued
| Ex. No. | E | Purity (%) | HPLC RT (min) | Mass (M + H) |
|---|---|---|---|---|
| 284 | 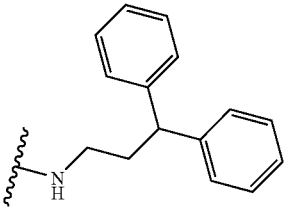 | 90.2% | 3.3 | 567.7 |
| 285 | 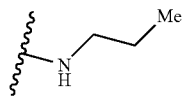 | 80.0% | 2.1 | 415.5 |
| 286 | 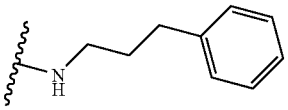 | 79.0% | 2.9 | 491.6 |
| 287 | 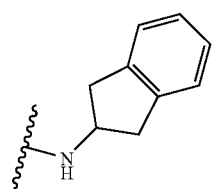 | 86.0% | 2.8 | 489.6 |
| 288 | 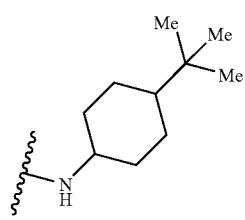 | 90.3% | 3.5 | 511.7 |
| 289 | 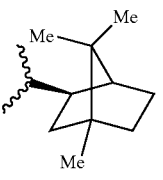 | 88.1% | 3.3 | 509.7 |
| 290 | 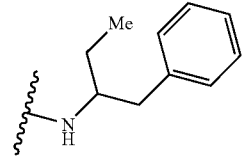 | 78.2% | 3.0 | 505.6 |
| 291 | 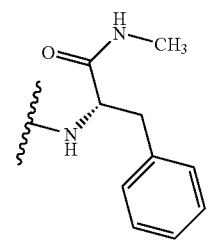 | 89.2% | 2.5 | 534.6 |

TABLE 8-continued

| Ex. No. | E | Purity (%) | HPLC RT (min) | Mass (M + H) |
| --- | --- | --- | --- | --- |
| 292 | 2-phenyl-norbornyl-NH- | 80.0% | 3.4 | 543.7 |
| 293 | 4-methylpiperazinyl | 85.5% | 1.3 | 456.5 |
| 294 | 4-benzylpiperazinyl | 87.9% | 1.9 | 532.6 |
| 295 | 4-[3-(dimethylamino)propyl]-piperazinyl (with Me on ring) | 78.3% | 1.4 | 527.7 |
| 296 | 4-isopropylpiperazinyl | 94.0% | 1.4 | 484.6 |
| 297 | 4-cyclopentylpiperazinyl | 86.5% | 1.7 | 510.6 |
| 298 | 4-(2-methoxyphenyl)-3-oxopiperazinyl | 95.5% | 2.3 | 562.6 |
| 299 | 4-(5,6,7,8-tetrahydroquinolin-8-yl)piperazinyl | 75.0% | 1.9 | 573.7 |
| 300 | 4-(6-methoxy-indanyl)piperazinyl | 87.8% | 2.2 | 588.7 |

TABLE 8-continued

| Ex. No. | E | Purity (%) | HPLC RT (min) | Mass (M + H) |
|---|---|---|---|---|
| 301 | | 84.9% | 1.9 | 524.7 |
| 302 | | 75.4% | 2.1 | 526.7 |
| 303 | | 91.8% | 2.5 | 595.7 |
| 304 | | 78.1% | 2.0 | 607.7 |
| 305 | | 90.5% | 2.2 | 590.7 |
| 306 | | 91.0% | 1.9 | 588.7 |

TABLE 8-continued
| Ex. No. | E | Purity (%) | HPLC RT (min) | Mass (M + H) |
|---|---|---|---|---|
| 307 | 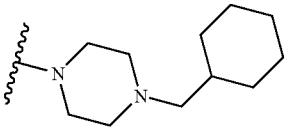 | 83.1% | 2.2 | 538.7 |
| 308 | 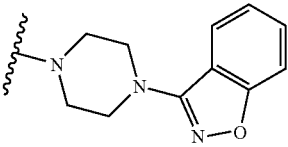 | 88.7% | 2.9 | 559.6 |
| 309 | 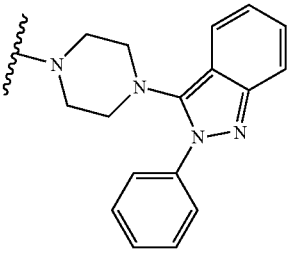 | 89.3% | 3.1 | 634.7 |
| 310 | 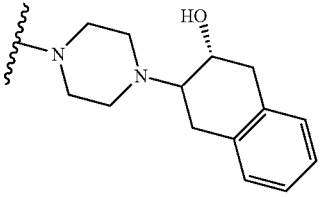 | 90.1% | 2.4 | 588.7 |
| 311 | 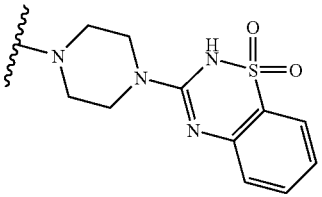 | 88.4% | 2.4 | 622.7 |

EXAMPLES 312–316

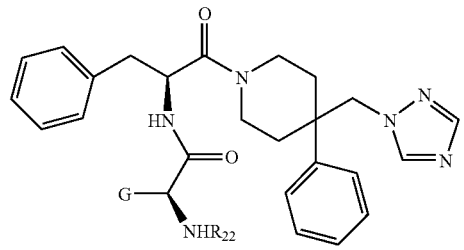

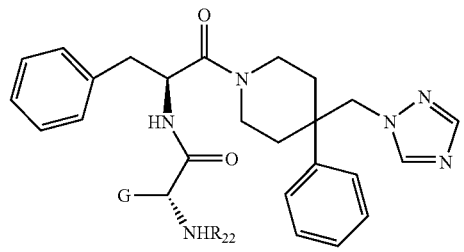

Compounds having the above formulae A or B, wherein G and $R_{22}$ have the values listed in Table 9, were prepared following the same or similar procedure as for Example 1.

TABLE 9

| Ex. No. | Core | G | $R_{22}$ | Purity (%) | HPLC RT (min) | Mass (M + H) |
|---|---|---|---|---|---|---|
| 312 | A | $H_2N$-C(O)-CH(CH$_3$)- | -C(CH$_3$)-C(O)-O-C(CH$_3$)$_2$ | 82.0% | 3.8 | 644.44 |
| 313 | A | Me-S-CH$_2$CH$_2$- | -C(CH$_3$)-C(O)-O-C(CH$_3$)$_2$ | 80.0% | 4.1 | 661.43 |
| 314 | B | N≡C-CH(CH$_3$)- | -C(CH$_3$)-C(O)-O-C(CH$_3$)$_2$ | 91.0% | 3.9 | 626.42 |
| 315 | A | $H_2N$-C(O)-CH$_2$CH$_2$- | -C(CH$_3$)-C(O)-O-CH$_3$ | 89.0% | 3.4 | 600.41 |
| 316 | B | $H_2N$-C(O)-CH$_2$CH$_2$- | -C(CH$_3$)-C(O)-O-C(CH$_3$)$_2$ | 94.1% | 3.8 | 658.44 |

EXAMPLE 317

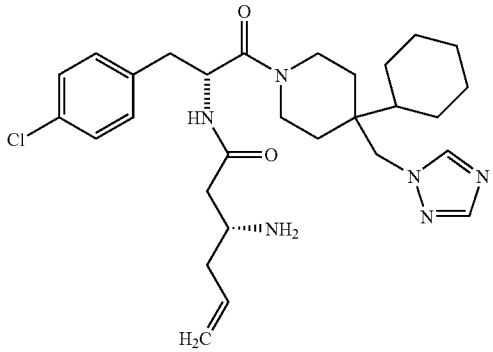

Step A:

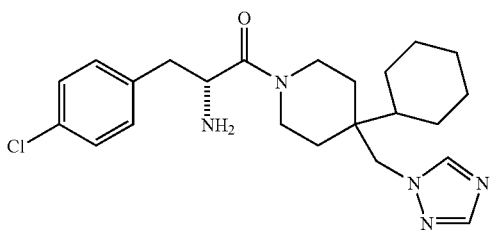

(317A)

Compound 317A was prepared by coupling of commercially available N-BOC D-4-chlorophenylalanine and 4-Cyclohexyl-4-[1,2,4]triazol-1-ylmethyl-piperidine, followed by deprotection of the BOC group, as described in WO 00/74679.

Step B:

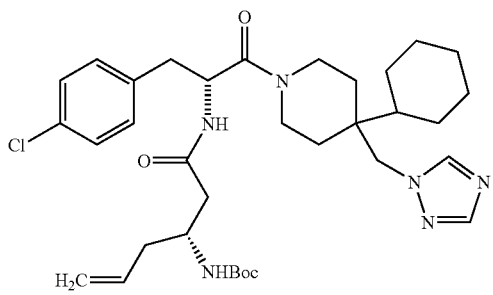

(317B)

To a solution of the compound 317A and the amino acid having the formula,

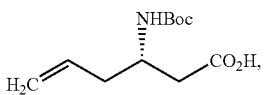

in DCM (12 mL) was added 1-ethyl-3-(3-dimethylaminopropyl) carbodiimide (736 mg, 3.8 mmol) and HOBt (518 mg, 3.8 mmol) at RT. The mixture was stirred at RT overnight and a sat'd solution of ammonium chloride (15 ML) was added. The separated aqueous layer was extracted with DCM (3×25 mL), and the combined organic layers were dried (MgSO$_4$ anh.), filtered, and evaporated to afford compound 317B which was used in the next step without purification. HPLC (Column: Combiscreen C8 S-5 4.6×50 mm; Flow rate: 4 mL/min, Solvent system: 0–100% B in 4 min. Solvent A: 10% CH$_3$CN—90% H$_2$O—0.1% TFA; Solvent B: 90% CH$_3$CN—10% H$_2$O—0.1% TFA; UV: 220 nm): retention time 2.40 min, purity 99.2%; HPLC (Column: Luna CN 4.6×30 mm; Flow rate: 4 mL/min, Solvent system: 0–100% B in 4 min. Solvent A: 10% CH$_3$CN—90% H$_2$O—5 mM NH$_4$OAc; Solvent B: 90% CH$_3$CN—10% H$_2$O—5 mM NH$_4$OAc; UV: 220 nm): retention time 3.06 min, purity 100%; HPLC/MS (Column: YMC ODS-A C18 4.6×50 mm; Flow rate: 4 mL/min, Solvent system: 0–100% B in 2 min. Solvent A: 10% CH$_3$CN—90% H$_2$O—5 mM NH$_4$OAc; Solvent B: 90% CH$_3$CN—10% H$_2$O—5 mM NH$_4$OAc; UV: 220 nm; Micromass ZMD 2000, ESI): retention time 1.81 min, purity 97.8%, MS pos. m/z 541 (M+H)$^+$; MS (Finigan TSQ 7000, ESI) m/z 541 (M+H)+; $^1$H NMR (400 MHz, CD$_3$OD) δ ppm (two rotamers; ratio 1.8:1) 8.45 (1H, s, minor rotamer), 8.43 (1H, s, major rotamer), 7.99 (1H, s, minor rotamer), 7.94 (1H, s, major rotamer), 7.31 (2H, d, J=8 Hz, major rotamer), 7.28 (2H, d, J=8 Hz, minor rotamer), 7.23 (2H, d, J=8 Hz, major rotamer), 7.21 (2H, d, J=8 Hz, minor rotamer), 5.82–5.69 (1H, m), 5.26–5.20 (2H, m), 5.05 (1H, dd, J=6, 12 Hz), 4.26 (2H, s, major rotamer), 4.25 (2H, s, minor rotamer), 3.69–3.58 (1H, m), 3.55–3.43 (2H, m), 3.40–3.32 (1H, m), 3.01–2.84 (2H, m), 2.63–2.55 (1H, m), 2.50–2.43 (1H, m), 2.37–2.30 (2H, m), 1.85–1.63 (6H, m), 1.45–0.86 (8H, m). $^{13}$C NMR (100.61 MHz, CD$_3$OD) δ ppm (two rotamers; ratio 1.8:1) 171.7 (s, major rotamer), 171.6 (s, minor rotamer), 171.3 (s), 151.7 (d), 146.4 (d), 136.7 (d, minor rotamer), 136.6 (d, major rotamer), 134.1 (s, major rotamer), 134.0 (d, minor rotamer), 132.8 (s, major rotamer). 132.7 (s, minor rotamer), 2×132.3 (d, major rotamer), 2×132.1 (d, minor rotamer), 2×129.8 (d, major rotamer), 2×129.7 (minor rotamer), 121.0 (t), 53.0 (t, minor rotamer), 52.7 (t, major rotamer), 51.6 (d, minor rotamer) 51.4 (d, major rotamer), 43.0 (d), 42.8 (t, minor rotamer), 42.6 (t, major rotamer), 39.1 (s), 2×38.9 (t, major rotamer), 38.7 (t, major rotamer), 38.3 (t, minor rotamer), 38.0 (s, major rotamer), 37.9 (s, minor rotamer), 37.1 (t, minor rotamer), 37.0 (t, major rotamer), 31.2 (t), 30.6 (t), 2×28.2 (t), 27.6 (t), 3×27.4 (t); ir (ν$_{max}$, KBr) cm$^{-1}$: 3565–2500 (broad), 1683, 1635, 1456, 1203, 1139.

Step C:

EXAMPLE 317

To a solution of Compound 317B in DCM (10 mL) was added a 20% (v/v) solution of TFA in DCM (1.6 mL) at RT. The mixture was stirred at RT for 8 h and evaporated under reduced pressure. The residue was purified using preparative HPLC and after evaporation, the residue was lyophilized to afford Example 317 as the TFA salt. HPLC ret. time (min) =1.54$^b$, MS (M+H)$^+$=541.

EXAMPLES 318–322

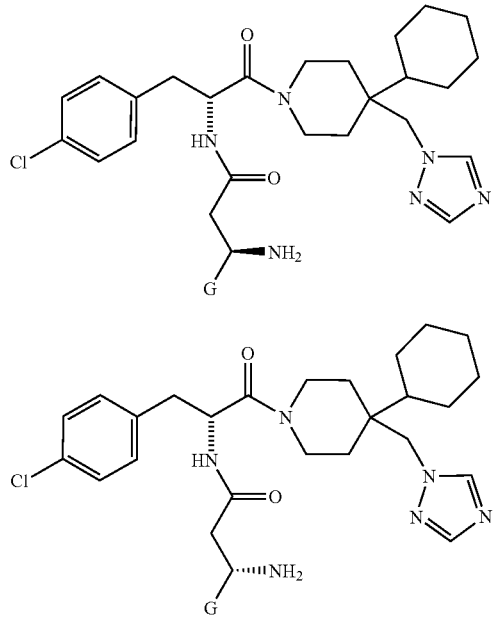

Compounds having the above formulae A or B. wherein G has the values listed in Table 10 were prepared following the same or similar procedure as for Example 1.

TABLE 10

| Ex. No. | Core | G | HPLC Retention Time (min) | MS Data[b] (M + H)+ |
|---|---|---|---|---|
| 318 | B | | 3.20[c] | 617 |
| 319 | A | | 3.19[c] | 617 |
| 320 | A | | 1.52[b] | 541 |
| 321 | A | CH₃SCH₂CH₂— | 1.74[a] | 575 |
| 322 | B | | 1.52[a] | 544 |

EXAMPLES 323–328

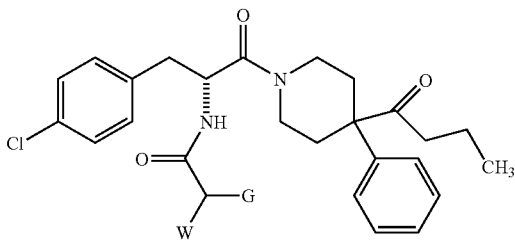

(Im)

Compounds of formula (Im), above, wherein the groups G and W have the values in Table 11, were prepared following the same or similar procedure described for Example 1, using a different amino acid in place of N-Boc-L-histidine in Step A.

TABLE 11

| Ex No. | G | W | Purity (%) | time (min) | Mass (M + H) |
|---|---|---|---|---|---|
| 323 | | | 91 | 2.5 | 549 |
| 324 | | | 86 | 2.56 | 549.31 |
| 325 | | | 88 | 2.49 | 549.3 |

TABLE 11-continued

| Ex No. | G | W | Purity (%) | time (min) | Mass (M + H) |
|---|---|---|---|---|---|
| 326 | | | 91 | 2.52 | 549.31 |
| 327 | | | 89 | 2.53 | 563.42 |
| 328 | | | 92 | 2.58 | 577.38 |

The invention claimed is:

1. A compound of formula (I),

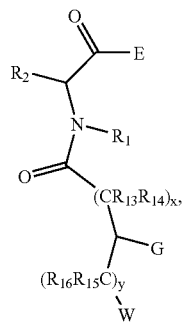

or a pharmaceutically-acceptable salt or hydrate, thereof, in which:

$R_1$ is hydrogen or $C_{1-6}$alkyl;

$R_2$ is $C_{1-6}$alkyl or $C_{2-6}$alkenyl optionally substituted with one to three aryl, cycloalkyl, or heteroaryl, provided that where G is —$NR_{18}CO_2R_{19}$, or when y is 0, $R_2$ is $C_{1-6}$alkyl or $C_{2-6}$alkenyl, each optionally substituted with heteroaryl;

E is

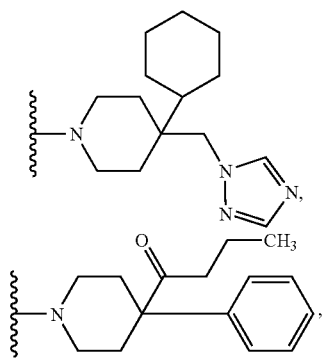

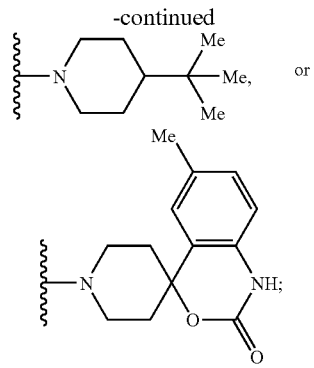

G is selected from —$NR_{18}C(=O)R_{19}$—$NR_{18}SO_2R_{17}$, —$NR_{18}CO_2R_{19}$, and —$NR_{20}C(=O)NR_{18}R_{19}$, or where G is —$NR_{18}CO_2R_{19}$, or when y is 0, $R_2$ is $C_{1-6}$alkyl or $C_{2-6}$alkenyl, each optionally substituted with heteroaryl;

W is selected from substituted or unsubstituted heterocyclo, or heteroaryl, selected from azetidinyl and imidazolyl, each optionally substituted with lower alkyl;

$R_{13}$, $R_{14}$, $R_{15}$ and $R_{16}$ are hydrogen;

$R_{17}$ is alkyl, substituted alkyl, cycloalkyl, aryl, heterocyclo, or heteroaryl;

$R_{18}$, $R_{19}$, and $R_{20}$ are independently selected from hydrogen, alkyl, substituted alkyl, alkenyl, substituted alkenyl, aryl, heteroaryl, cycloalkyl, heterocyclo, or $C(=O)R_{28}$; or when G is $NH(C=O)R_{19}$, $R_{19}$ may be a bond joined to W to define a heterocyclo ring; provided, however, that when y is at least one, W is imidazolyl, and G is —$NR_{18}C(=O)R_{19}$, then $R_{19}$ is not a $C_1$-alkyl having the substituent —$NR_{29}R_{31}$;

x is 0, 1, or 2; and y is 0, 1, 2, 3 and 4.

2. A compound according to claim 1, or a pharmaceutically-acceptable salt or hydrate, thereof, in which:

G is —$NR_{18}C(=O)R_{19}$;

$R_{17}$ is $C_{1-4}$alkyl, $C_{5-6}$cycloalkyl, phenyl or benzyl;

$R_{18}$, $R_{19}$, and $R_{20}$ are independently selected from hydrogen, $C_{1-4}$alkyl, phenyl, benzyl, $C_{5-6}$cycloalkyl, —C(=O)CH_2(phenyloxy), —C(=O)CH_2(benzyloxy), imidazolyl, pyridyl, furyl, thienyl, or $C_{1-4}$alkyl or $C_{2-4}$alkenyl substituted with one of phenyl, pyridyl, furyl, cyclopentyl, cyclohexyl, $CO_2Me$, phenyloxy, or benzyloxy, wherein each ringed group of $R_{18}$, $R_{19}$, and $R_{20}$ in turn is optionally substituted with one to two $R_{36}$, and/or optionally has a benzene ring or five membered heterocyclo having two oxygen atoms fused thereto; and $R_{36}$ is halogen, methoxy, nitro, phenyl, phenyloxy, or alkylamino.

3. A compound according to claim 2, or a pharmaceutically-acceptable salt or hydrate, thereof, in which $R_{18}$ is hydrogen or lower alkyl, and $R_{19}$ is $C_{1-4}$alkyl, $C_{2-4}$alkenyl, phenyl, benzyl, $C_{5-6}$cycloalkyl, —C(=O)CH$_2$(phenyloxy), —C(=O)CH$_2$(benzyloxy), imidazolyl, pyridyl, furyl, thienyl, or $C_{1-4}$alkyl or $C_{2-4}$alkenyl substituted with one of phenyl, phenyl, pyridyl, furyl, cyclopentyl, cyclohexyl, $CO_2Me$, phenyloxy, and benzyloxy, wherein each ringed group of $R_{19}$ in turn is optionally substituted with one to two $R_{36}$, and/or optionally has a benzene ring or five membered heterocyclo having two oxygen atoms fused thereto.

4. A compound according to claim 2, or a pharmaceutically-acceptable salt or hydrate, thereof, in which W is azetidinyl or imidazolyl.

5. A compound according to claim 1, or a pharmaceutically-acceptable salt or hydrate, thereof, having the formula:

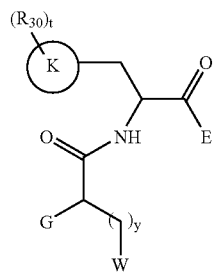

in which

K is phenyl or thiazolyl;

$R_{30}$ is selected from $C_{1-4}$alkyl, hydroxy, alkoxy, halogen, nitro, cyano, amino, alkylamino, phenyl, and —C(=O) phenyl;

t is 0, 1 or 2; and y is 0, 1 or 2.

6. A compound according to claim 1, or a pharmaceutically-acceptable salt or hydrate, thereof, in which W is a ring selected from:

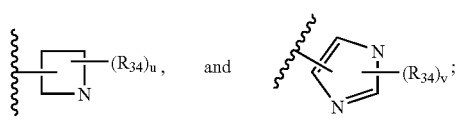

$R_{34}$ at each occurrence is attached to any available carbon or nitrogen atom of W and is selected from $C_{1-6}$alkyl u is selected from 0, 1, 2, and 3; and v is 0, 1 or 2.

7. A compound according to claim 1, or a pharmaceutically-acceptable salt or hydrate, thereof, in which $R_2$ is selected from, $C_{1-6}$alkyl, $C_{2-6}$alkenyl, $C_{2-6}$alkenylene-K, and —CH$_2$)$_g$—K;

K is selected from phenyl, napthyl, thienyl, thiazolyl, pyridinyl, pyrimidinyl, and $C_{5-6}$cycloalkyl, wherein each group K in turn is optionally substituted with one to three $R_{30}$ or has a benzene ring fused thereto, which also may be substituted with one to three $R_{30}$;

$R_{30}$ is selected from $C_{1-4}$alkyl, hydroxy, alkoxy, halogen, nitro, cyano, amino, alkylamino, phenyl, and acylphenyl; and g is 0, 1, 2 or 3.

8. A compound according to claim 1, or a pharmaceutically-acceptable salt or hydrate, thereof, in which —N(R$_1$)—CH(R$_2$)— taken together are selected from,

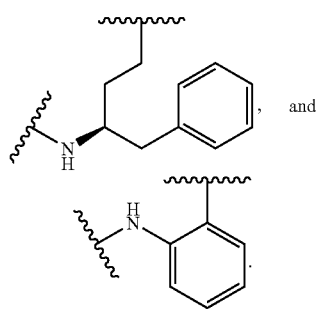

9. A compound according to claim 1, or a pharmaceutically-acceptable salt or hydrate, thereof, in which $R_1$ is hydrogen or $C_{1-4}$alkyl.

10. A compound having the formula,

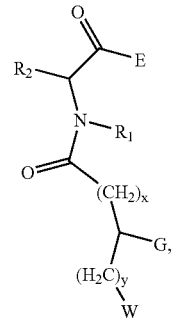

or a pharmaceutically-acceptable salt or hydrate, thereof, in which:

$R_1$ is hydrogen or $C_{1-6}$alkyl;

$R_2$ is $C_{1-6}$alkyl or $C_{2-6}$alkenyl optionally substituted with one to three-aryl, cycloalkyl, or heteroaryl, provided that where G is $C_{2-6}$alkenyl, or [A$_1$]—NR$_{18}$CO$_2$R$_{19}$, or when y is 0, $R_2$ may be or $C_{1-6}$alkyl or $C_{2-6}$alkenyl, each optionally substituted with heteroaryl;

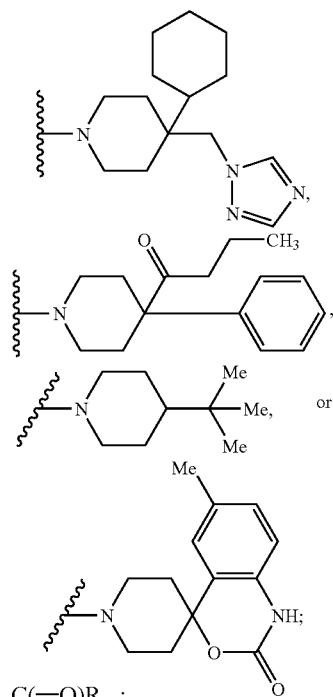

G is NR$_{18}$C(=O)R$_{19}$;

W is selected from -substituted or unsubstituted heterocyclo, or heteroaryl, selected from azetidinyl and imidazolyl, each optionally substituted with lower alkyl;

R$_{17}$ is alkyl, substituted alkyl, cycloalkyl, aryl, heterocyclo, or heteroaryl;

R$_{18}$, R$_{19}$, and R$_{20}$ are independently selected from hydrogen, alkyl, alkenyl, aryl, heteroaryl, cycloalkyl, heterocyclo, C(=O)R$_{28}$ or a C$_{1-4}$alkyl or C$_{2-4}$alkenyl substituted with one or more of aryl, heteroaryl, cycloalkyl, heterocyclo, alkoxycarbonyl, phenyloxy, and/or benzyloxy, and each of said ringed groups of R$_{18}$, R$_{19}$, and R$_{20}$ in turn is optionally substituted with one to two R$_{36}$;

R$_{21}$ and R$_{22}$ are selected from alkyl and substituted alkyl;

R$_{36}$ is halogen, methoxy, nitro, phenyl, phenyloxy, or alkylamino;

x is 0, 1, or 2; and y is 0, 1, 2, 3 or 4.

11. A compound according to claim 10, or a pharmaceutically-acceptable salt or hydrate, thereof, in which E is

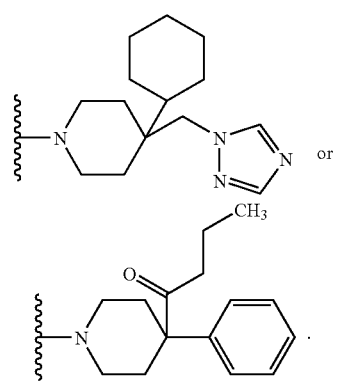

12. A compound according to claim 10, or a pharmaceutically-acceptable salt or hydrate, thereof, in which G is NHC(=O)(alkyl) or NHC(=O)phenyl.

13. A compound according to claim 1, having the formula,

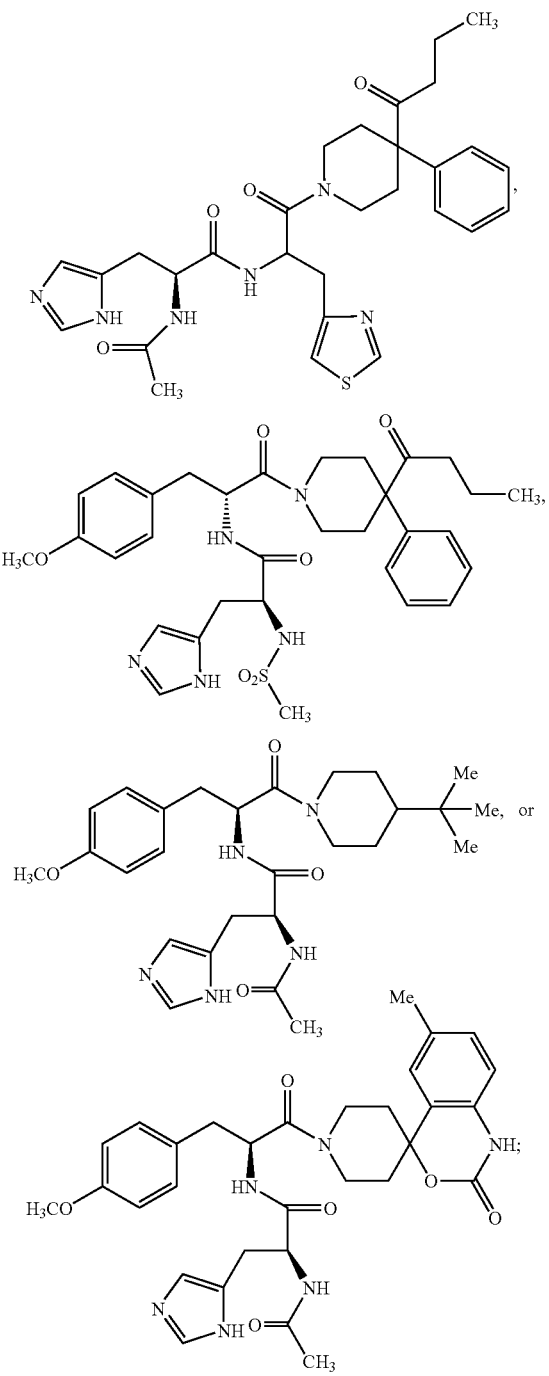

or a pharmaceutically-acceptable salt or hydrate, thereof.

14. A pharmaceutical composition comprising at least one compound according to claim 1 or a pharmaceutically-acceptable salt or hydrate, thereof; and a pharmaceutically-acceptable carrier or diluent.

* * * * *